(12) United States Patent
Kohchi et al.

(10) Patent No.: US 6,849,709 B2
(45) Date of Patent: *Feb. 1, 2005

(54) AEROTHRICIN DERIVATIVES

(75) Inventors: Masami Kohchi, Fujisawa (JP); Kazunao Masubuchi, Yokohama (JP); Takeshi Murata, Chigasaki (JP); Takehiro Okada, Fujisawa (JP); Nobuo Shimma, Chigasaki (JP)

(73) Assignee: Basilea Pharmaceutica AG (CH)

( * ) Notice: Subject to any disclaimer, the term of this patent is extended or adjusted under 35 U.S.C. 154(b) by 147 days.

This patent is subject to a terminal disclaimer.

(21) Appl. No.: 09/760,949

(22) Filed: Jan. 16, 2001

(65) Prior Publication Data

US 2001/0031728 A1 Oct. 18, 2001

(30) Foreign Application Priority Data

Jan. 17, 2000 (EP) .............................. 00100807

(51) Int. Cl.$^7$ .............................. C07K 7/50; C07K 7/08; C07K 7/06; A61K 38/10; A61K 38/12
(52) U.S. Cl. .................. 530/317; 530/321; 530/323; 530/332; 514/11; 514/14; 514/9; 435/71.1; 435/254.1; 435/911
(58) Field of Search .............................. 530/317, 321, 530/323, 332; 514/11, 14, 9; 435/71.1, 254.1, 911

(56) References Cited

U.S. PATENT DOCUMENTS

| | | | | |
|---|---|---|---|---|
| 5,547,934 A | | 8/1996 | Fujie et al. .................... | 514/11 |
| 6,489,440 B1 | * | 12/2002 | Aoki et al. .................. | 530/317 |
| 2001/0038824 A1 | * | 11/2001 | Horii et al. .................... | 424/43 |

FOREIGN PATENT DOCUMENTS

| | | |
|---|---|---|
| EP | 584 360 B1 | 3/1994 |
| EP | 736 541 A1 | 10/1996 |
| WO | 96/30399 | 10/1996 |
| WO | 00/05251 | 2/2000 |

OTHER PUBLICATIONS

David Barrett et al., Fujisawa Pharmaceuticals, "Synthesis and Biological Activity of Novel 1,3-beta-Glucan Synthase Inhibitors Derived from FR 9014690, an Antifungal Antibiotic", 19$^{th}$ Symposium of Medicinal Chemistry, 8$^{th}$ Annual Meeting of Division of Medicinal Chemistry Abstract 2P-14, p. 123 (1999).

* cited by examiner

Primary Examiner—Robert A. Wax
Assistant Examiner—Chih-Min Kam
(74) Attorney, Agent, or Firm—Gibbons, Del Deo, Dolan, Griffinger & Vecchione

(57) ABSTRACT

The present invention relates to novel Aerothricins represented by the Formula (I),

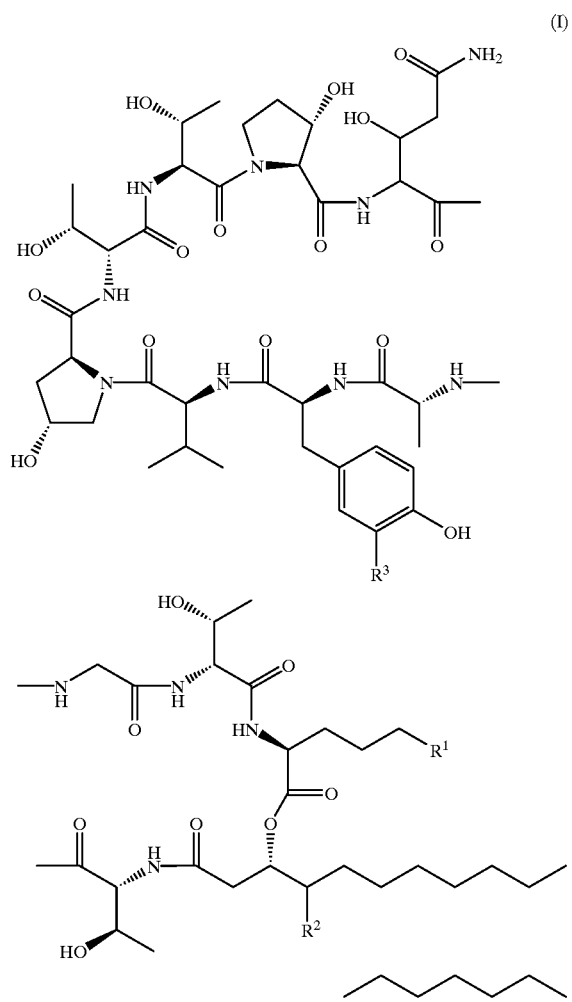

and pharmaceutically acceptable salts thereof.

The present invention also relates to a pharmaceutical composition comprising an Aerothricin of the Formula (I) and a pharmaceutically acceptable carrier. Furthermore, the present invention relates to the use of such Aerothricins for the preparation of medicaments, as well as to processes for the preparation of the Aerothricins of the Formula (I).

13 Claims, 8 Drawing Sheets

AEROTHRICIN DERIVATIVES

BACKGROUND OF THE INVENTION

The present invention relates to novel cyclic compounds having antifungal activity (hereinafter referred to as Aerothricins), the use of Aerothricins in the medical therapy, pharmaceutical compositions containing Aerothricins as well as to processes for the preparation of Aerothricins.

Azole antifungal agents are currently widely used for the treatment of systemic mycoses. However, long term prophylactic use of azole antifungals resulted in generation of azole resistant *Candida* spp. due to their fungistatic action. Therefore, fungicidal agents are particularly important for treatment of severe systemic mycoses, especially against pulmonary aspergillosis. Furthermore, the currently available antifungal agents are not effective against *Scedosporium* spp. which is one of the emerging pathogens among immunocompromised patients. Amphotericin B is a highly effective fungicidal agent currently used clinically, but its therapeutic index (effective dose vs. toxic dose) is rather narrow. Certain cyclic compounds such as LY303366 (EP 736 541), WF11243 (EP 584 360) are known to show fungicidal activity through inhibition of β-1,3-glucan synthase. However, they have still some disadvantages in terms of antifungal spectrum and/or safety profile. Thus, development of new fungicidal agents with better safety profile and efficacy against major systemic pathogens including *Aspergillus fumigatus* and *Scedosporium* spp. is urgently required.

SUMMARY OF THE INVENTION

The present invention relates to novel derivatives of Aerothricins which are useful as anti-fungal agents and to the processes for preparing such derivatives. More particularly, the Aerothricin derivatives of the present invention may be usefully employed in the topical and systems treatment of fungal infections in animals as well as humans. The present invention also relates to pharmaceutical composition containing the disclosed Aerothricin derivatives and methods for the propylactic and/or therapeutic treatment of infectious diseases utilising such compositions.

DETAILED DESCRIPTION OF THE INVENTION

Figure 1:
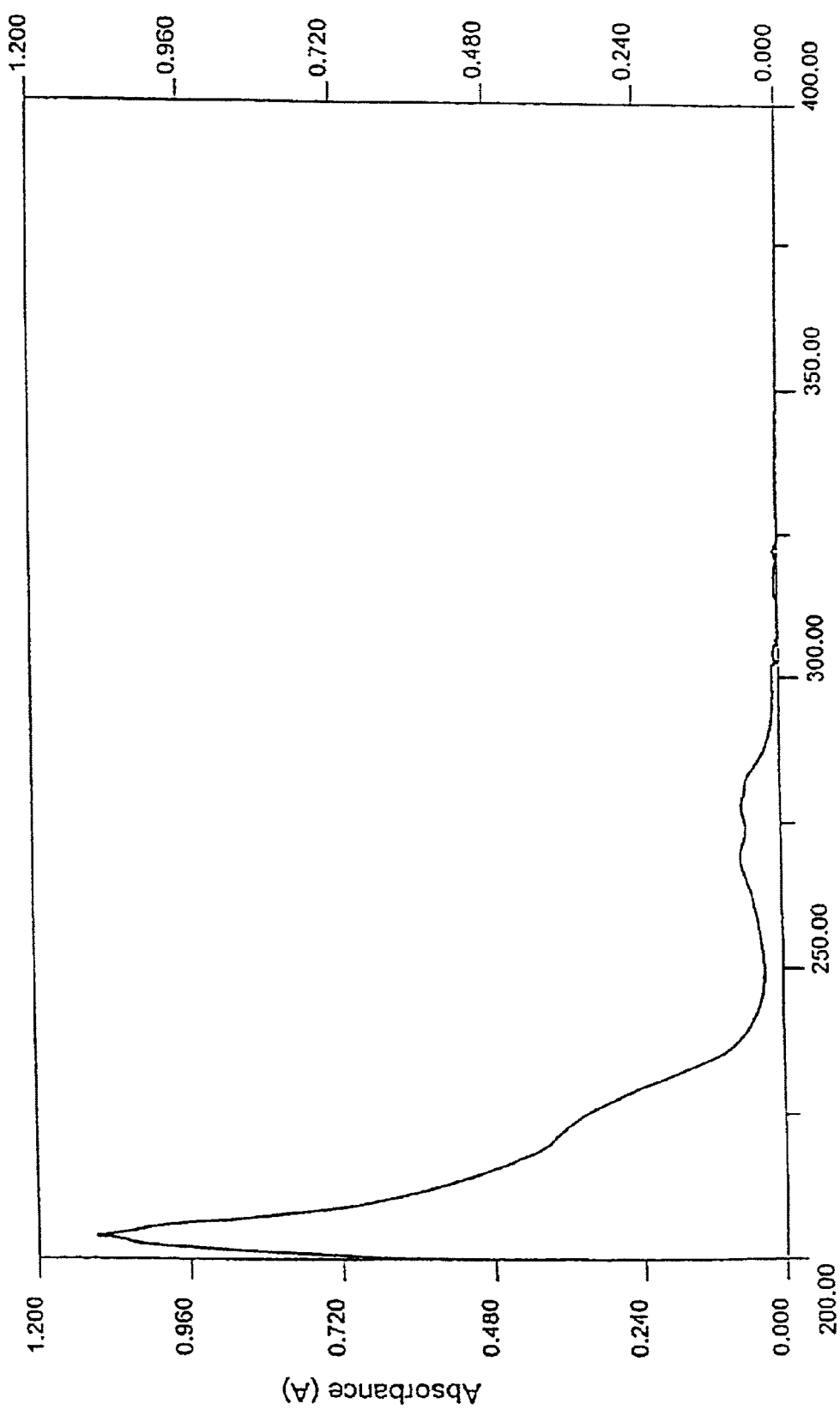
FIGS. 1–4 respectively show the UV, IR, $^1$H-NMR and $^{13}$C-NMR spectra plotted for the starting material Aerothricin 1 prepared in accordance with Reference Example 1.

The present invention relates to novel Aerothricins represented by the Formula (I):

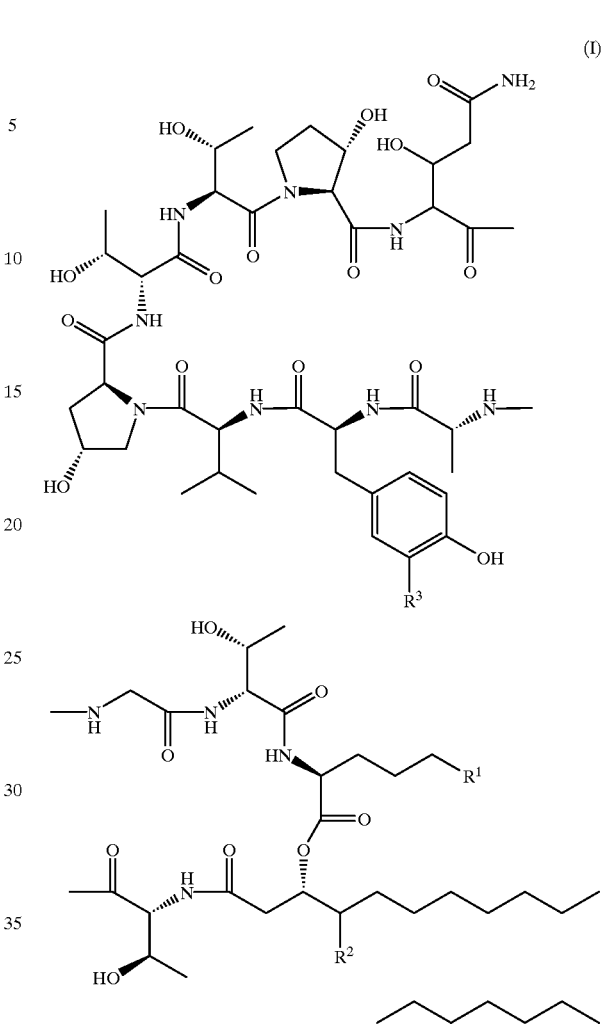

wherein $R^1$ is N-(3-aminopropyl)-N-[(2S)-2,5-diaminovaleryl]amino, N-(3-aminopropyl)-N-[5-amino-2-[N,N-bis(2-aminoethyl)amino]valeryl]amino, N-(3-aminopropyl)-N-[5-amino-2-[N-(3-aminopropyl)amino]valeryl]amino, N-(2-aminoethyl)-N-[5-amino-2-[N,N-bis(2-aminoethyl)amino]valeryl]amino or ornityl-ornitylamino;

$R^2$ is hydrogen or methyl;

$R^3$ is hydrogen or hydroxy;

and pharmaceutically acceptable salts thereof.

The present invention also relates to a pharmaceutical composition comprising an Aerothricin of Formula (I) and a pharmaceutically acceptable carrier. Furthermore, the present invention relates to the use of such Aerothricins for the preparation of medicaments, as well as to processes for the preparation of the Aerothricins of Formula (I). Additionally, the present invention relates to a method for the prophylactic and/or therapeutic treatment of infectious diseases caused by pathogenic microorganisms.

In a preferred embodiment, the present invention relates to Aerothricins of Formula (I), wherein $R^1$ is N-(3-aminopropyl)-N-[(2S)-2,5-diaminovaleryl]amino, N-(3-aminopropyl)-N-[(2S)-5-amino-2-[N,N-bis(2-aminoethyl)amino]valeryl]amino, N-(3-aminopropyl)-N-[(2R)-5- amino-2-[N,N-bis(2-aminoethyl)amino]valeryl]amino, N-(3-aminopropyl)-N-[(2S)-5-amino-2-[N-(3-aminopropyl)amino]valeryl]amino, N-(2-aminoethyl)-N-[(2S)-5-amino-2-[N,N-bis(2-aminoethyl)amino]valeryl]amino or (L)-ornityl-(D)-ornitylamino; $R^2$ is hydrogen or methyl, preferably hydrogen; $R^3$ is hydrogen or hydroxy, preferably hydrogen; and pharmaceutically acceptable salts thereof.

In another preferred embodiment, the present invention relates to a compound of Formula (I), wherein $R^1$ is N-(3-aminopropyl)-N-[(2S)-2,5-diaminovaleryl]amino, and $R^2$ and $R^3$ are hydrogen atoms; namely of the Formula (IIIa):

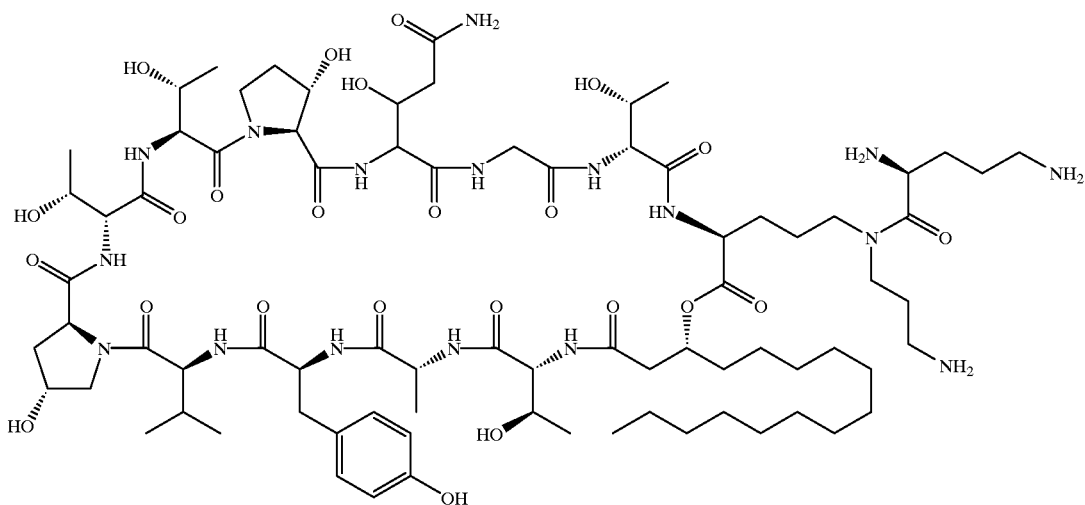

(IIIa)

and pharmaceutically acceptable salts thereof.

In another preferred embodiment, the present invention relates to a compound of the Formula (I), wherein $R^1$ is (L)-ornityl-(D)-ornitylamino, and $R^2$ and $R^3$ are hydrogen atoms; namely of the Formula (IVa):

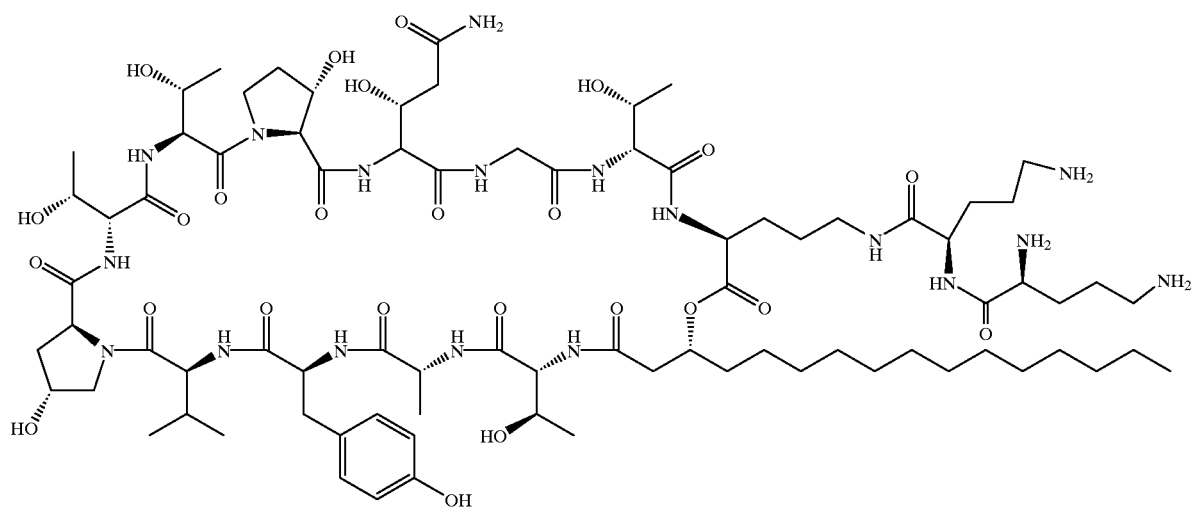

(IVa)

and pharmaceutically acceptable salts thereof.

In another preferred embodiment, the present invention relates to a compound of Formula (I), wherein $R^1$ is N-(3-aminopropyl)-N-[(2S)-5-amino-2-[N,N-bis(2-aminoethyl)amino]valeryl]amino, and $R^2$ and $R^3$ are hydrogen atoms; namely of the Formula (Va):

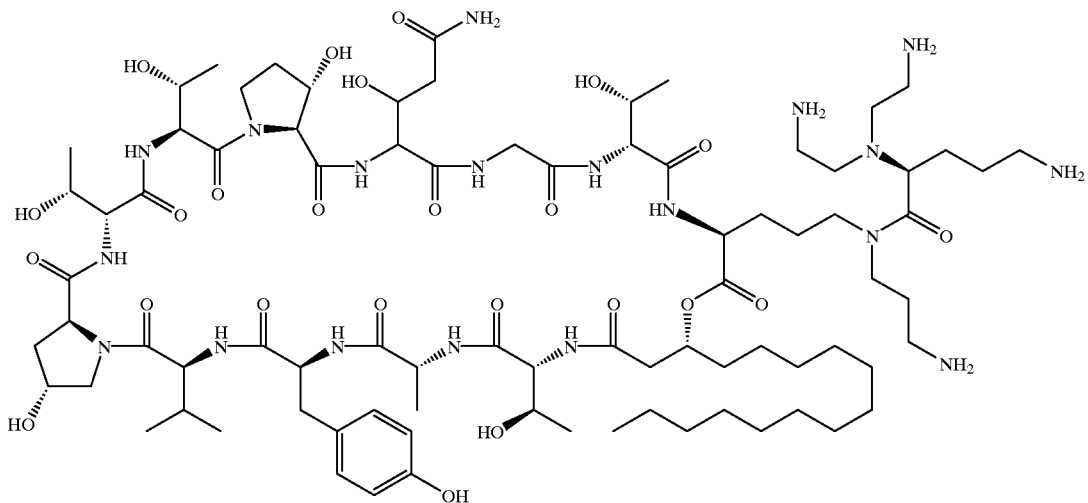

(Va)

and pharmaceutically acceptable salts thereof.

In another preferred embodiment, the present invention relates to a compound of Formula (I), wherein $R^1$ is N-(3-aminopropyl)-N-[(2R)-5-amino-2-[N,N-bis(2-aminoethyl)amino]valeryl]amino, and $R^2$ and $R^3$ are hydrogen atoms; namely of the Formula (VIa):

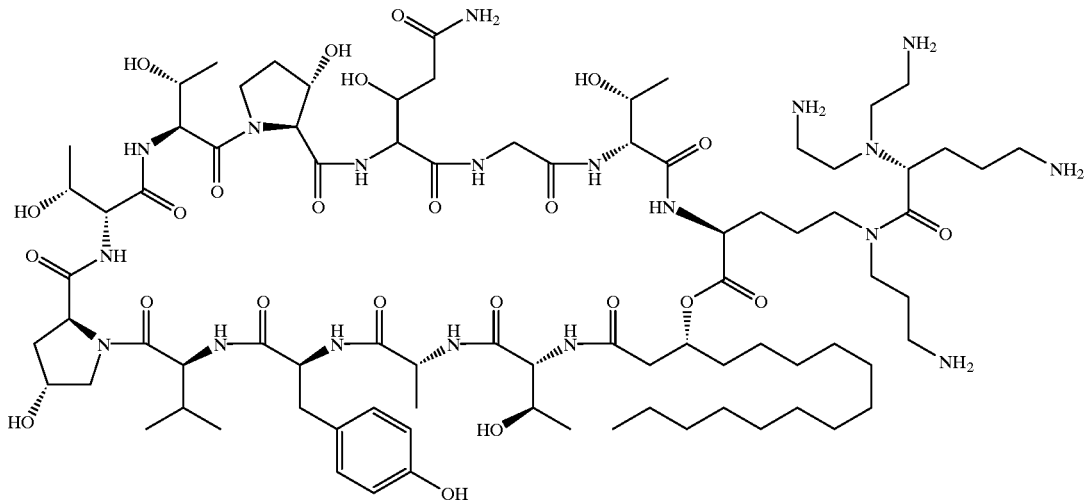

(VIa)

and pharmaceutically acceptable salts thereof.

In another preferred embodiment, the present invention relates to a compound of Formula (I), wherein $R^1$ is N-(3-aminopropyl)-N-[(2S)-5-amino-2-[N-(3-aminopropyl)amino]valeryl]amino, and $R^2$ and $R^3$ are hydrogen atoms; namely of the Formula (VIIa):

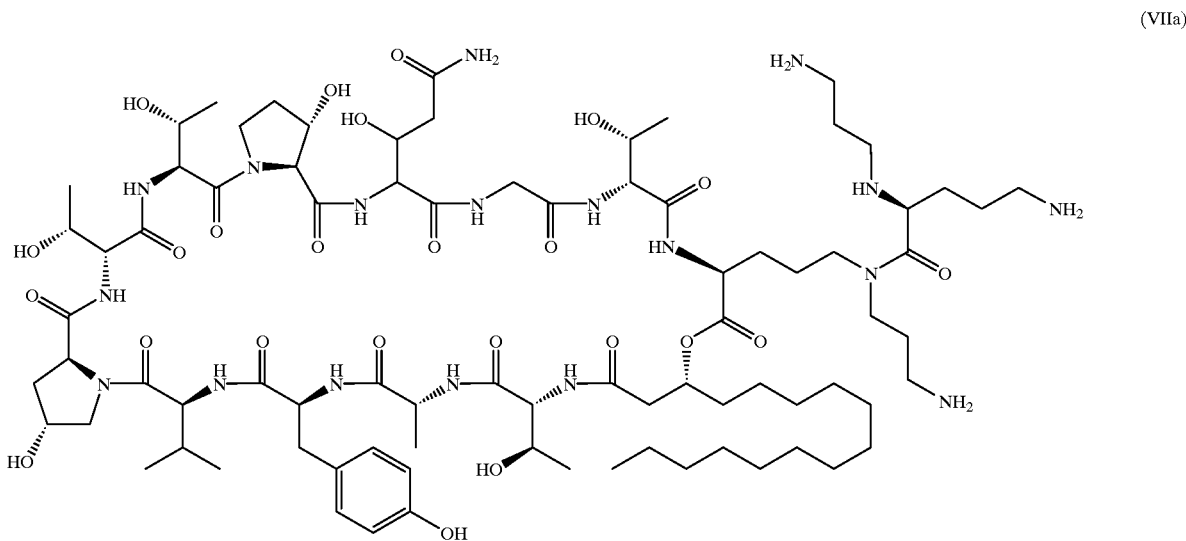

(VIIa)

and pharmaceutically acceptable salts thereof.

In another preferred embodiment, the present invention relates to a compound of Formula (I), wherein $R^1$ is N-(2-aminoethyl)-N-[(2S)-5-amino-2-[N,N-bis(2-aminoethyl)amino]valeryl]amino, and $R^2$ and $R^3$ are hydrogen atoms; namely of the Formula (VIIIa):

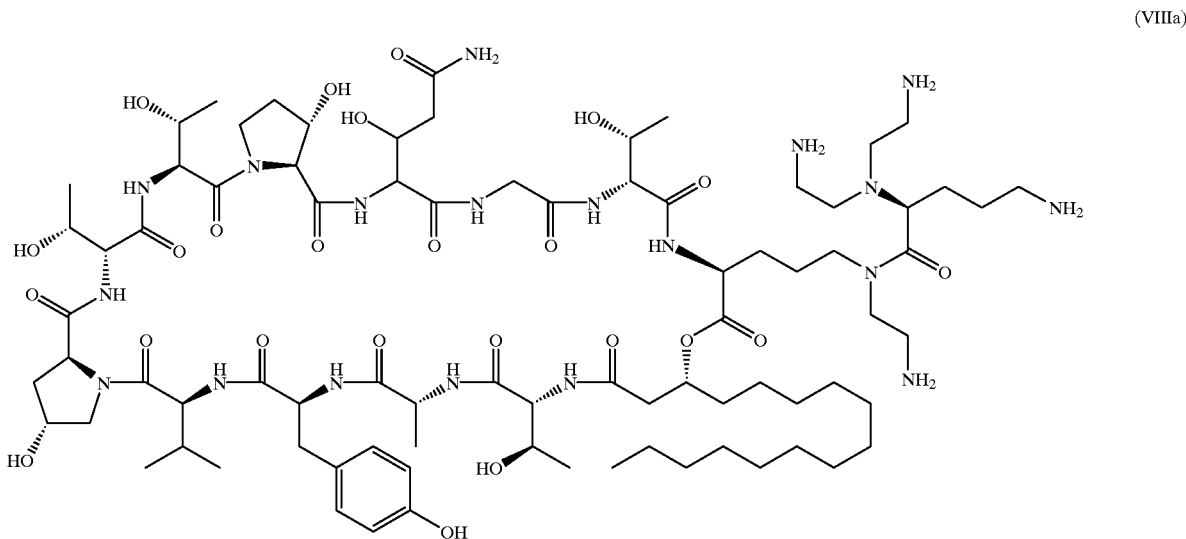

(VIIIa)

and pharmaceutically acceptable salts thereof.

Aerothricins in accordance with the present invention are Aerothricins exemplified in the following Table 1.

TABLE 1

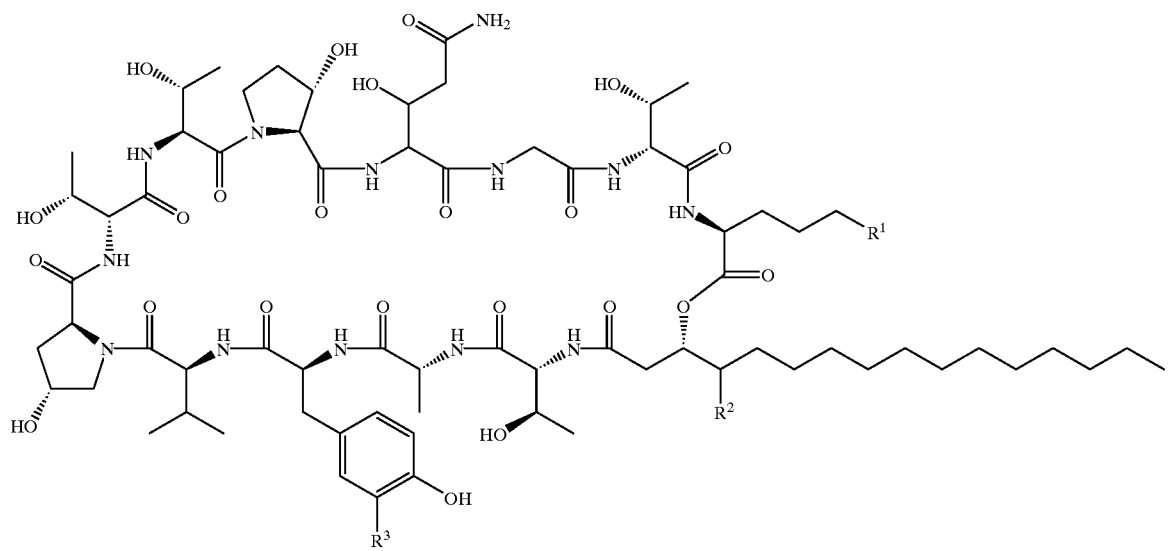

(I)

| Compound name | R¹ | R² | R³ |
|---|---|---|---|
| Aerothricin 1 (starting material) | NH$_2$ | CH$_3$ | H |
| Aerothricin 2 (starting material) | NH$_2$ | H | OH |
| Aerothricin 3 (starting material) | NH$_2$ | H | H |
| Aerothricin 132 | —NCO—**CH(NH$_2$)—(CH$_2$)$_3$NH$_2$<br>\|<br>(CH$_2$)$_3$NH$_2$ | H | H |
| Aerothricin 133 | —NCO—*CH(CH$_2$)$_3$NH$_2$<br>\|       \|<br>H    NHCO**CH(CH$_2$)$_3$NH$_2$<br>                   \|<br>                   NH$_2$ | H | H |
| Aerothricin 134 | —NCO—**CH—(CH$_2$)$_3$NH$_2$<br>\|    \|<br>     N[(CH$_2$)$_2$NH$_2$]$_2$<br>(CH$_2$)$_3$NH$_2$ | H | H |
| Aerothricin 135 | —NCO—*CH—(CH$_2$)$_3$NH$_2$<br>\|    \|<br>     N[(CH$_2$)$_2$NH$_2$]$_2$<br>(CH$_2$)$_3$NH$_2$ | H | H |
| Aerothricin 136 | —NCO—**CH—(CH$_2$)$_3$NH$_2$<br>\|    \|<br>     NH(CH$_2$)$_3$NH$_2$<br>(CH$_2$)$_3$NH$_2$ | H | H |
| Aerothricin 137 | —NCO—**CH—(CH$_2$)$_3$NH$_2$<br>\|    \|<br>     N[(CH$_2$)$_2$NH$_2$]$_2$<br>(CH$_2$)$_2$NH$_2$ | H | H |

*(R) configuration, **(S) configuration

Aerothricins represented by Formula (I) can be produced from Aerothricin 1, 2 or 3 according to the methods outlined in scheme 1 and 2, wherein amino protecting group $P_1$ and $P_2$ can be selected from tert-butoxycarbonyl (Boc), benzyloxycarbonyl (Cbz), fluorenylmethoxycarbonyl (Fmoc) and the like; $R^2$ and $R^3$ are as defined above.

Process A

The starting compounds, Aerothricins of the Formula (II), can be produced by cultivating a microorganism belonging to Deuteromycotina capable of producing Aerothricins 1, 2 and 3 [Aerothricin 3 (=WF11243) is described in Reference Example 1] under aerobic conditions in an aqueous or a solid medium and isolating Aerothricins 1, 2 and/or 3 from the culture.

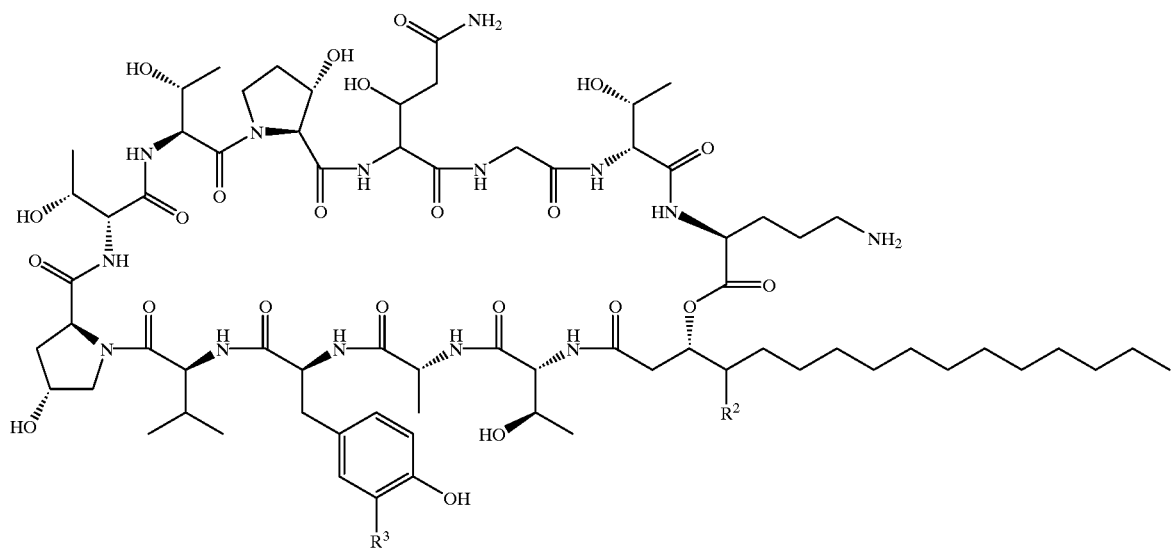

(II)

[wherein $R^2$ is hydrogen or methyl; $R^3$ is hydrogen or hydroxy]

The compounds of Formula II can be converted into compounds of Formula I by the following processes B or C:

Scheme 1

Process B

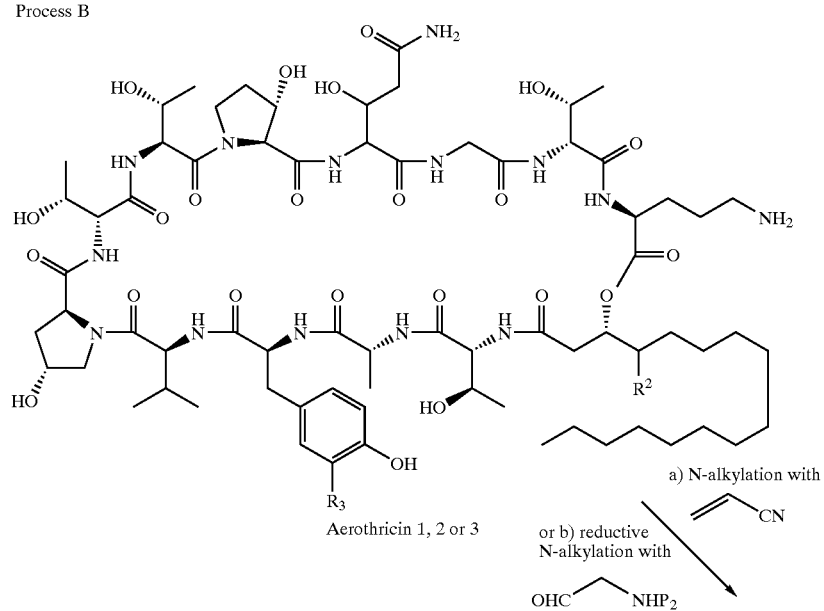

Aerothricin 1, 2 or 3 a) N-alkylation with or b) reductive N-alkylation with

-continued
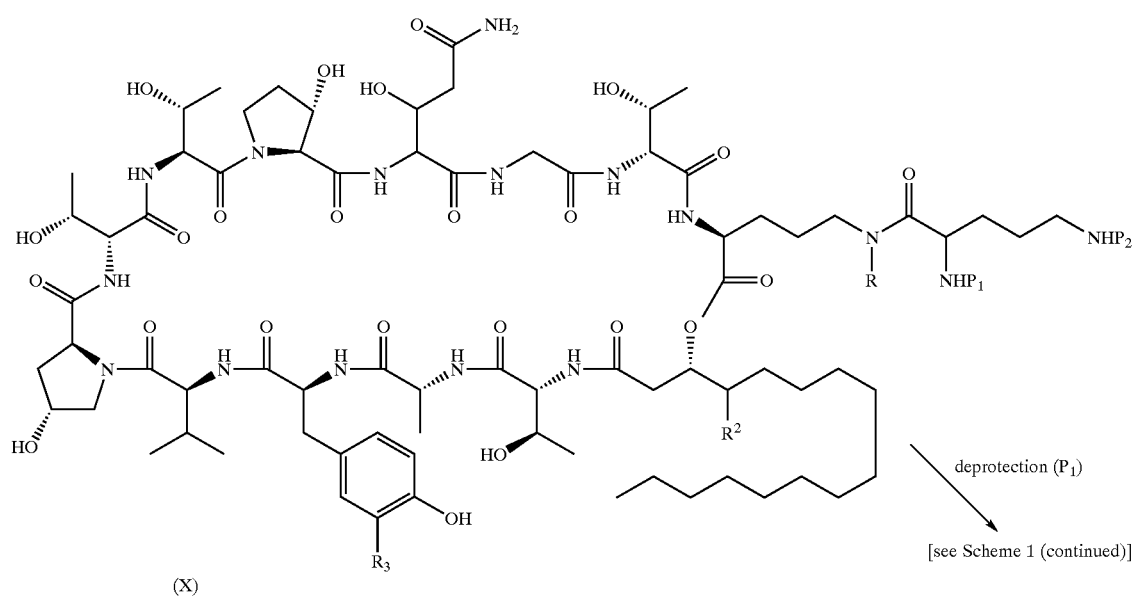
(X)
1) deprotection (P₁ and P₂)
2) reduction of CN [R = (CH₂)₂CN]
deprotection (P₁)
[see Scheme 1 (continued)]
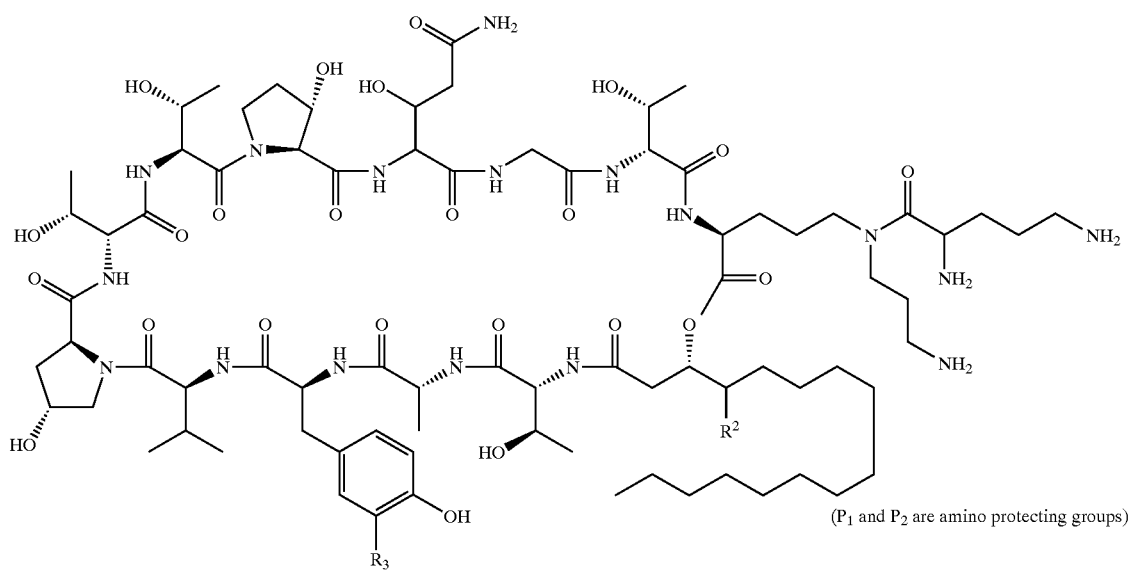
(III)
(P₁ and P₂ are amino protecting groups)
Compound (X)
[see Scheme 1]
deprotection (P₁)

-continued
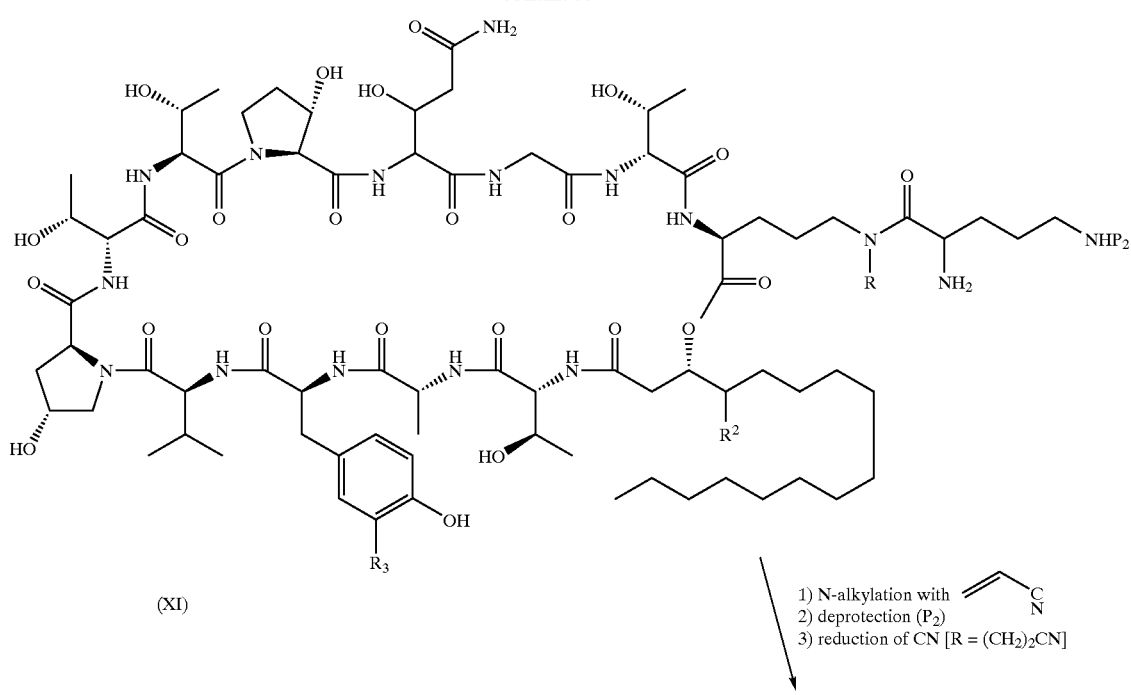
(XI)
1) N-alkylation with ![acrylonitrile]
2) deprotection (P₂)
3) reduction of CN [R = (CH₂)₂CN]
1) reductive alkylation with
   OHC—NHP₂
2) deprotection (P₂),
   followed by reduction of
   CN [when R = CH₂₂CN]
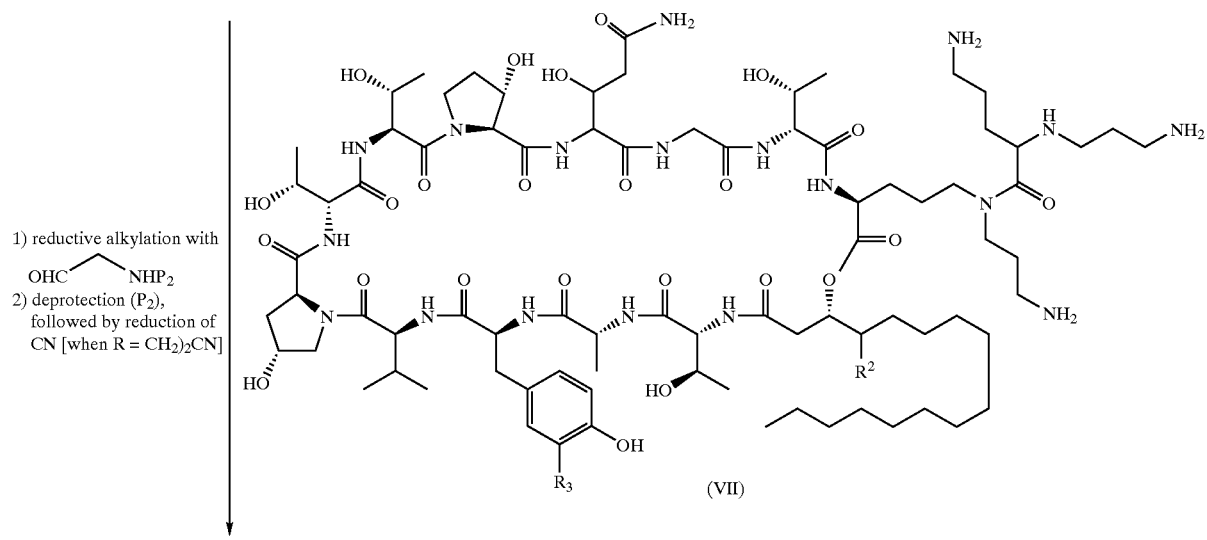
(VII)

-continued
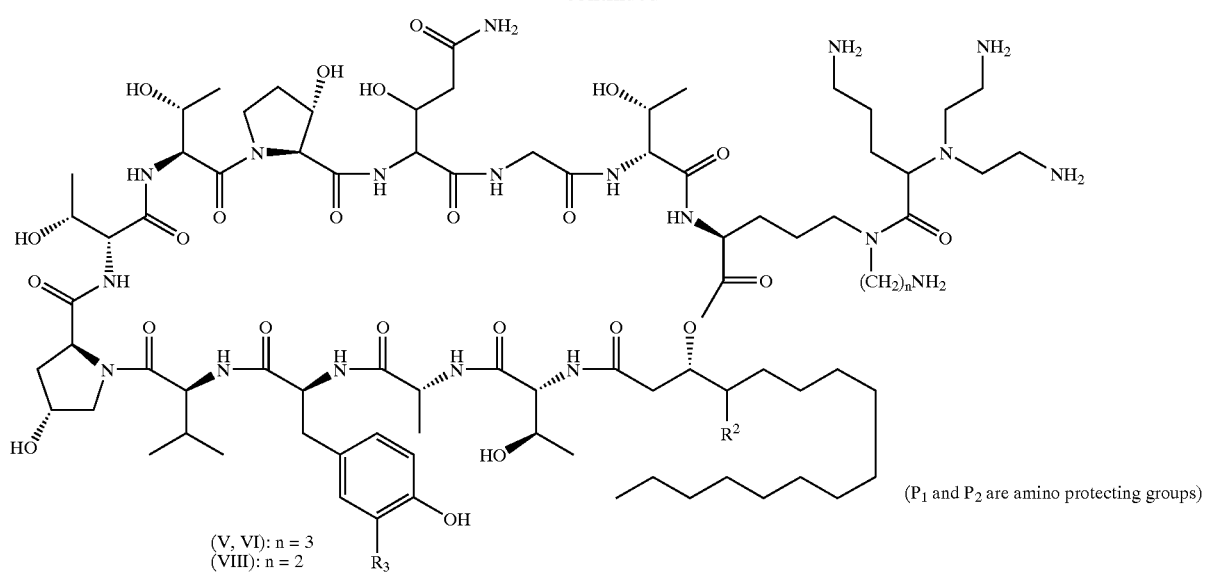
(V, VI): n = 3
(VIII): n = 2
(P₁ and P₂ are amino protecting groups)
Scheme 2
Process C
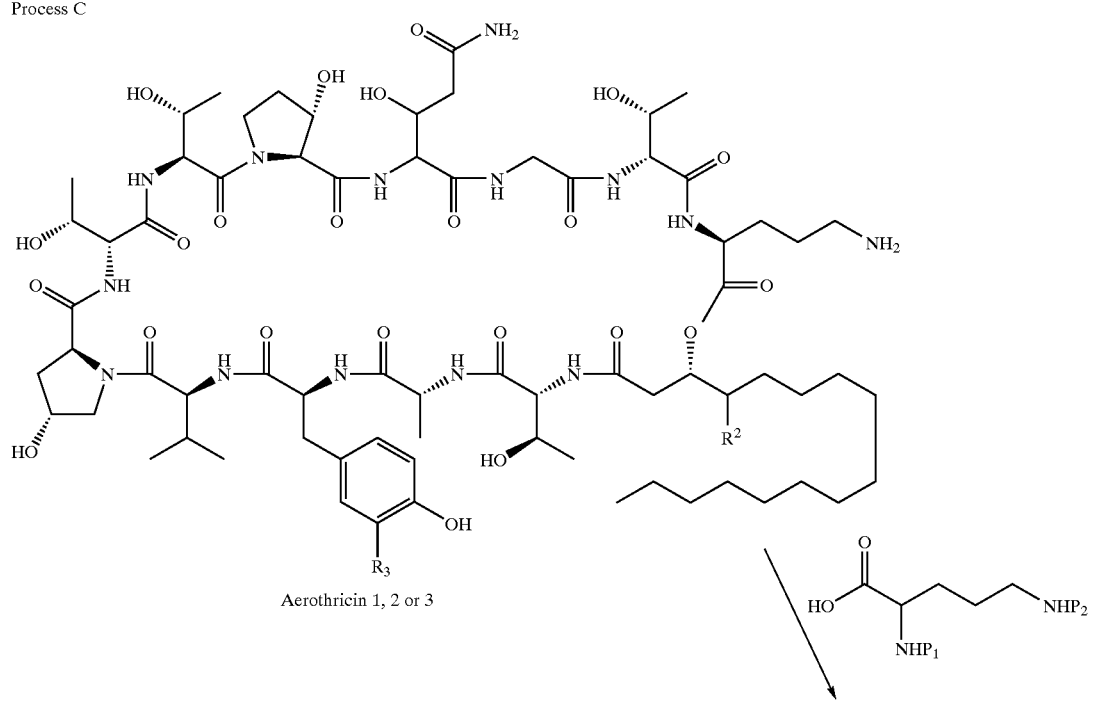
Aerothricin 1, 2 or 3

-continued
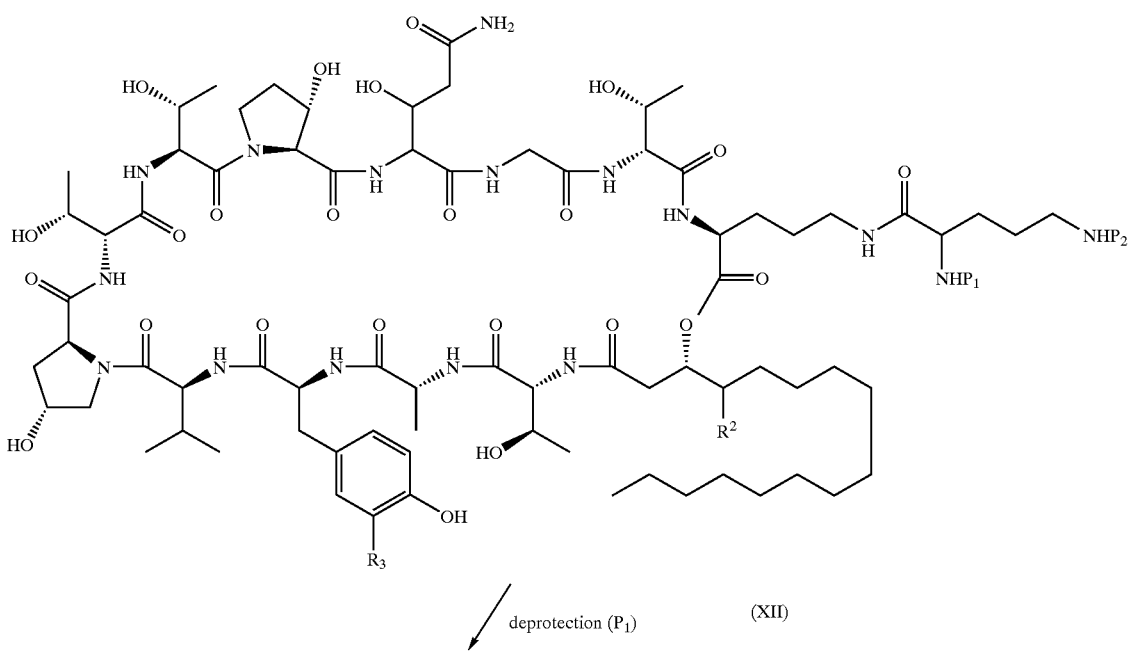
(XII)
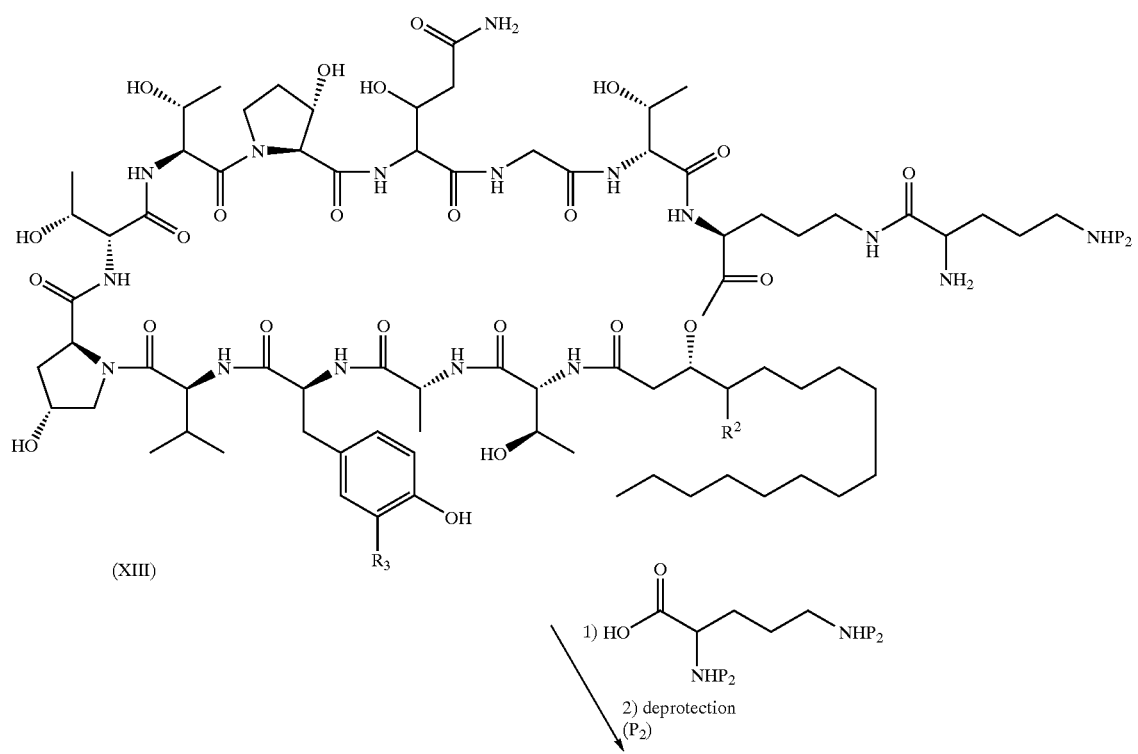
(XIII)

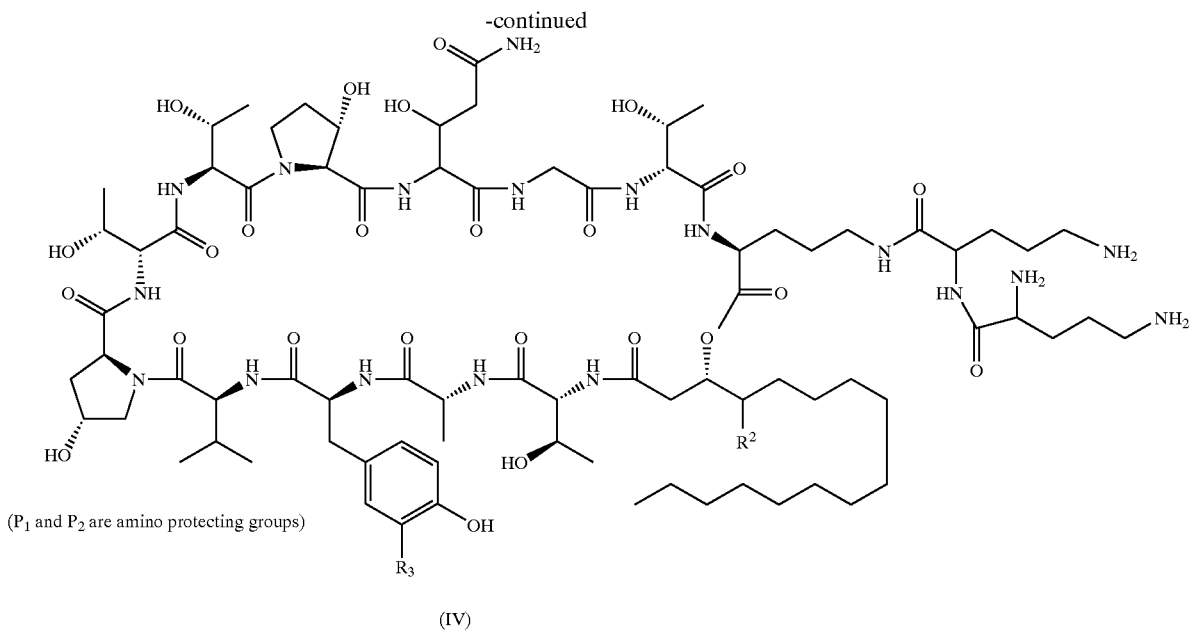

(P₁ and P₂ are amino protecting groups)

(IV)

The Processes A to C can be illustrated in more detail as follows:

Process A

The microorganism used in the present invention can be any strains including mutants and variants belonging to Deuteromycotina capable of producing Aerothricins 1, 2 and 3. Especially preferred is strain NR 7379 which was isolated from fallen leaves collected at Kagoshima pref. in Japan, and identified as a strain belonging to Deuteromycotina.

The cultural and morphological characteristics of strain NR 7379 are as follows:

1. Cultural Characteristics

Corn meal agar (CMA): Growth was not extensive. The colonies reached 11 mm in diameter from inoculum (4.5 mm diam. agar plug) after 14 days at 25° C. They were plane and pale cream yellow. The reverse side was pale cream yellow. Colorless and mucilaginous exudates were present.

Miura's medium (LCA): Growth was not extensive. The colonies reached 11 mm in diameter from inoculum after 14 days at 25° C. They were plane and pale cream yellow. The reverse side was pale cream yellow. Exudates were absent.

Malt extract agar (MEA): Growth was not extensive. The colonies were pustuliform and attained a diameter of 18 mm from inoculum after 14 days at 25° C. The color of colonies was light yellowish brown. The reverse side was of the same color. Exudates were colorless and mucilaginous.

Potato-dextrose agar (PDA): Growth was not extensive. The colonies were pustuliform and reached 14 mm in diameter from inoculum after 14 days at 25° C. The color and texture of colonies were similar to those on MEA. Exudates were colorless and mucilaginous.

Germination was observed between 5° C. and 30° C. on CMA, LCA, MEA, and PDA.

2. Morphological Characteristics

Mycelia were partly immersed, partly superficial, branched, septate, and pale brown to cream yellow. Conidiophores were formed from immersed mycelium. They were hyaline, septate, branched, irregular. Conidiogenous cells were on distinct conidiophores or irregular hyphae. They were enteroblastic, phialidic, terminal or subterminal. Terminal or subterminal phialides were variable in length and shape. They were cylindrical to lageniform and their length and width were up to 5.5 to 10 μm and 2.5 to 5.5 μm respectively. Irregularly filiform Conidiophores with lateral conidiogenous cells immediately below septa were often formed. Conidia were one-celled, hyaline, smooth, globose to subglobose, 2.0 to 5.5 μm in length and 2.0 to 5.0 μm in width.

On the basis of these distinct cultural and morphological characteristics, the present strain belonged to Deuteromycotina designated as Deuteromycotina NR 7379.

The strain denoted as Deuteromycotina NR 7379 has been deposited with the National Institute of Bioscience and Human-Technology, Agency of Industrial Science and Technology, Japan in the name of Nippon Roche K.K., of 6-1, Shiba 2-chome, Minato-ku Tokyo, 105 Japan on Jun. 16, 1998 under the Budapest Treaty as follows: Deuteromycotina NR 7379 (FERM BP-6391).

The cultivation in accordance with the process provided by the present invention can be carried out in a culture medium which contains customary nutrients usable by the microorganism being cultivated. As carbon sources there can be mentioned, for example, glucose, sucrose, starch, glycerol, molasses, dextrin and mixtures thereof. Nitrogen sources are, for example, soybean meal, cottonseed meal, meat extract, peptone, dried yeast, yeast extract, corn steep liquor, ammonium sulfate, sodium nitrate and mixtures thereof. Moreover, there may be added to the culture medium other organic or inorganic substances for promoting the growth of the microorganism and for increasing the production of Aerothricin 1. Examples of such substances are inorganic salts, such as calcium carbonate, sodium chloride, phosphates and the like.

The cultivation is carried out under aerobic conditions preferably in a liquid medium by submerged fermentation, or in a solid medium by static fermentation. A temperature of 20° C. to 30° C., with an optimal temperature of 27° C. is suitable for cultivation. The cultivation is preferably carried out at a pH of 3 to 9. The cultivation time depends on the conditions under which the cultivation is carried out. In general, it is sufficient to carry out the cultivation for 20 to 360 h.

For harvesting the objective Aerothricins 1, 2 and 3 from the cultures, separation methods which are usually employed to isolate metabolites produced by microbes from their cultures can be properly used. For example, Aerothricin 1, which is a methanol extractable amphoteric substance, is recovered advantageously by the following procedures.

That is, the whole culture solid obtained by solid state fermentation is extracted with an appropriate solvent to recover the proposed product. The solvents which can be used to extract the objective compound from the whole cultured solid include water-soluble organic solvents or hydrous solutions of water-soluble organic solvents, such as methanol, ethanol and hydrous alcohols.

For removing salts, water soluble substances, etc. from the resulting extract, use is made of, with advantage, solvent partition between water and water-immiscible organic solvents, such as n-butanol, ethyl acetate, etc. For removing coloring substances, fat-soluble substance or the like from the extract, use is made of, with advantage, solvent purification by methanol, ethanol, a mixture of acetonitrile-0.1% aqueous trifluoroacetic acid, etc.

For complete purification of Aerothricins, column chromatography is used with advantage. Carriers which can be used in such a column chromatography are such as YMC-GEL ODS (Yamamura Chemical Laboratories, Japan) or Preparative C18 (Waters Millipore Corporation). As an eluent, use is made of a solvent system consisting a mixture of aqueous trifluoroacetic acid and appropriate water-soluble organic solvents such as methanol, ethanol, acetonitrile, etc. The eluate fraction thus purified, which contains each component, can be subjected to concentration or freeze-drying to pulverize Aerothricins 1, 2 and 3.

Aerothricins 1, 2 and 3 were isolated as a trifluoroacetic acid salt, but the free Aerothricins 1, 2 and 3 can be prepared by the following procedure. Namely, Aerothricins 1, 2 and 3 trifluoroacetic acid salt are dissolved in water, to which was added one equivalent of sodium hydroxide, and the mixture is subjected to Sephadex LH-20 column Chromatography, followed by elution with a hydrous alcohol such as methanol-water, etc. to thereby obtain Aerothricins 1, 2 and 3 (free form), respectively.

Process B

The compound of Formula (III) can be prepared from Aerothricins of Formula (II) [wherein $R^1$ is an amino group; $R^2$ and $R^3$ are as defined above] in 4 steps: (1) N-alkylation with acrylonitrile, (2) acylation with N-protected ornitine, (3) removal of amino protecting groups ($P_1$ and $P_2$), and (4) reduction of cyano group.

The compound of Formula (V, VI) can be prepared from Aerothricins of Formula (II) [wherein $R^1$ is an amino group; $R^2$ and $R^3$ are as defined above] in 6 steps: (1) N-alkylation with acrylonitrile, (2) acylation with N-protected ornitine, (3) removal of amino protecting group ($P_1$), (4) reductive N-alkylation with N-protected amino-acetaldehyde, (5) removal of amino protecting group ($P_2$), and (6) reduction of cyano group.

The compound of Formula (VIII) can be prepared from Aerothricins of Formula (II) [wherein $R^1$ is an amino group; $R^2$ and $R^3$ are as defined above] in 6 steps: (1) reductive N-alkylation with N-protected amino-acetaldehyde, (2) acylation with N-protected ornitine, (3) removal of amino protecting group ($P_1$), (4) reductive N-alkylation with N-protected amino-acetaldehyde, (5) removal of amino protecting group ($P_1$), and (6) reduction of cyano group.

The compound of Formula (VII) can be prepared from Aerothricins of Formula (II) [wherein $R^1$ is an amino group; $R^2$ and $R^3$ are as defined above] in 6 steps: (1) N-alkylation with acrylonitrile, (2) acylation with N-protected ornitine, (3) removal of amino protecting group ($P_1$), (4) N-alkylation with acrylonitrile, (5) removal of amino protecting group ($P_2$), and (6) reduction of cyano group.

Process C

The compound of Formula (IV) can be prepared from Aerothricins of Formula (II) [wherein $R^1$ is an amino group; $R^2$ and $R^3$ are as defined above] in 4 steps: (1) acylation with N-protected ornitine, (2) removal of amino protecting group ($P_1$), (3) acylation with N-protected ornitine, and (4) removal of amino protecting group ($P_2$).

In the above processes B and C;

(a) N-monoalkylation of an amino group can be done using acrylonitrile according to the method described in Organic Synthesis col. Vol. III, page 93.

(b) N-alkylation of the primary or secondary amino group can be done by the conventional reductive alkylation with N-protected aminoacetaldehyde using a reducing agent such as sodium cyanoborohydride in the presence or absence of weak acid such as acetic acid. The reaction can be carried out at room temperature in a solvent such as methanol, ethanol, acetic acid and the like.

(c) The reduction of the nitrile group can be achieved by catalytic hydrogenation or reduction with sodium borohydride/cobalt chloride, borane-methylsulide complex and the like [cf. J. Med. Chem., 37, 222 (1994)].

(d) N-acylation of an amino group can be done with N-protected ornitine using condensation agents such as dicyclohexylcarbodiimide, BOP, HBTU, TNTU, PyBroP™, PYBOP™, TBTU, TSTU, HOBt and the like, or the combination of two of them. The reaction can be carried out in a solvent such as methanol, ethanol, pyridine, N,N-dimethylformamide, N-methylpyrrolidone and the like in the presence or absence of a base such as triethylamine, di-isopropylethylamine, pyridine and the like at a temperature between −20° C. and +50° C., preferably at 0° C. to +25° C.

(e) The removal of the amino protecting group can be done by the method known to those skilled in the art, e.g. treatment with trifluoroacetic acid for Boc group, or piperidine for Fmoc group.

The present invention is also concerned with acid addition salts of Aerothricins. The acid addition salt can be obtained as trifluoroacetic acid salt after normal course of isolation. The salt thus obtained may be dissolved in water and passed through an anion exchange column bearing the desired anion. The eluate containing the desired salt may be concentrated to recover the salt as a solid product.

The Aerothricins of Formula (I) may be converted to a corresponding salt by virtue of the presence of the tertiary nitrogen atoms.

The acid addition salt of Aerothricins of Formula (I) can be obtained by treatment of the free base of Aerothricins with at least a stoichiometric amount of an appropriate acid, such as mineral acids, e.g., hydrochloric acid, hydrobromic acid, sulfuric acid, nitric acid, phosphoric acid, and the like, and organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Typically, the free base is dissolved in an inert organic solvent such as ethanol, methanol, and the like, and the acid added in a similar solvent. The temperature is maintained at about 40° C. The resulting salt precipitates spontaneously or may be brought out of solution with a less polar solvent.

The acid addition salts of the Aerothricins of Formula (I) maybe converted to the corresponding free base by treatment with at least a stoichiometric amount of a suitable base such as sodium or potassium hydroxide, potassium carbonate, sodium bicarbonate, ammonia, and the like.

Aerothricins provided by the present invention exhibit broad fungicidal activity against various fungi and can be used as agents for treatment and prophylaxis of fungal infectious diseases. The in vitro and in vivo antifungal activity (see Tables 2, 3-1 and 3-2) as well as the toxicity to hepatocytes (see Table 4) of the representative Aerothricins of Formula (I) are shown as follows:

1. In vitro Antifungal Activities

The in vitro antifungal activities of the representative Aerothricins of the present study were evaluated by determining the 80% inhibitory concentration ($IC_{80}$), which was calculated as the lowest concentration of an antifungal to inhibit the growth of fungus to 20% turbidity compared with the drug-free control growth spectrophotometrically.

The $IC_{80}$ values were determined by the broth microdilution procedure based on NCCLS Approved Standard with the following minor modifications (National Committee for Clinical Laboratory Standards. (1997) Reference method for broth dilution antifungal susceptibility testing for yeasts. Approved standard. Document M27-A). Yeast Nitrogen Base (YNB; Difco Lab.) supplemented with 1% glucose and 0.25% $K_2HPO_4$ was used as testing medium for yeasts, the same medium solidified with 0.2% low melting point agarose (BRL) was used for filamentous fungi. Inoculum size was $1–3 \times 10^3$ cells/ml, and incubation was performed for 1–2 days at 35° C.

TABLE 2

In vitro Antifungal activity, $IC_{80}$ (µg/ml)

|  | Candida albicans CY1002 | Aspergillus fumigatus CF1003 | Scedosporium apiospermum CF1077 |
|---|---|---|---|
| Aerothricin 132 | 0.28 | 2.9 | 0.38 |
| Aerothricin 134 | 0.37 | 0.58 | 0.37 |
| Aerothricin 135 | 0.41 | 0.37 | 0.35 |
| Aerothricin 136 | 0.33 | 0.38 | 0.34 |

2. In vivo Antifungal Efficacy 2-1: Murine Systemic Candidiasis

In vivo antifungal efficacy of Aerothricins of the present invention against systemic candidiasis is shown in the following Table 3-1. Mice of a conventional immunocompetent mouse strain, Crj: CD- 1 (ICR) were used for experimental infection models of systemic candidiasis. 4 weeks old Crj: CD-1 (ICR) mice were used for systemic candidiasis by injecting Candida albicans $5 \times 10^6$ conidia/mouse via the tail vein. Test compounds were intravenously (i.v.) given once just after infection for systemic candidiasis. 50% of effective dose ($ED_{50}$) values were calculated from the survival number at each dose on day 7.

TABLE 3-1

In vivo antifungal activity against systemic candidiasis in mice, $ED_{50}$ (mg/kg) on day 7

| Aerothricin 132 | 0.43 |
|---|---|
| Aerothricin 133 | 0.35 |
| Aerothricin 135 | 0.35 |

2-2: Murine Pulmonary Aspergillosis

In vivo antifungal efficacy of Aerothricins of the present invention against pulmonary aspergillosis is shown in the following Table 3-2. Murine pulmonary aspergillosis was created in cortisone-treated (250 mg/kg, twice subcutaneous treatments on 3 days before and on the infection day) ICR male mouse. Conidia of A. fumigatus ($2.5 \times 10^5$ conidia/mouse) were infected intratracheally to these mice, and treatments were carried out once daily for 4 days. The efficacy of each drug was determined from the survival number, and 50% of effective dose ($ED_{50}$) was calculated from the survival number at each dose on the 14 days.

TABLE 3-2

In vivo antifungal activity against pulmonary aspergillosis in mice, $ED_{50}$ (mg/kg) on day 14

| Aerothricin 132 | 5.2 |
|---|---|
| Aerothricin 134 | 5.8 |
| Aerothricin 137 | 5.2 |
| Aerothricin 3 | >15 |

3. In vitro Hepatotoxicity Test

The mouse hepatocytes were isolated by a collagenase digestion and cultured in microtest plates. The hepatocyte monolayers were exposed to the test Aerothricins in the culture system for 1 day. After the culture period, the hepatocytes were observed under a microscope and evaluated morphologically. The degree of the morphological alteration (degeneration) of the hepatocytes by the test Aerothricins were compared with WF11243 and LY303366.

TABLE 4

| Cytotoxicity to hepatocyte (µg/ml) | |
|---|---|
| Aerothricin 132 | >100 |
| Aerothricin 134 | >100 |
| Aerothricin 135 | >100 |
| WF11243 (= Aerothricin 3) | 100 |
| LY303366 | 10 |

5 mg/kg and 30 mg/kg of Aerothricin 132 administration (once daily: i.v.) to mice for 2 weeks showed no acute toxicity.

Therefore, the novel Aerothricins of Formula (I) as well as pharmaceutically acceptable salts thereof exhibit potent antifungal activity against various fungal infections, including Aspergillosis, in mice over a wide range of dosages and are useful as antifungal agents. Moreover, the Aerothricins provided by this invention are much less cytotoxic to hepatocytes than the known cyclic peptide derivatives (WF11243 and LY303366).

Aerothricins of the present invention may also be useful for inhibiting or alleviating Pneumocystis carinii infections in immune-compromised patients.

The present invention further relates to the pharmaceutical compositions containing the novel Aerothricins of Formula (I) as well as pharmaceutically acceptable salts thereof.

The novel Aerothricins of Formula (I) as well as pharmaceutically acceptable salts thereof are highly active fungicidal agents. They are active against a variety of fungal species including Candida spp., Aspergillus spp., Scedosporium spp, Mucor spp. and Absidia spp.

Thus, Aerothricins of the present invention are useful for topical and systemic treatment of mycoses in animals as well as humans. For example, they are useful in treating topical and mucosal fungal infections caused by Candida spp., Trichophyton spp., and Microsporum spp. They may also be used in the treatment of systemic fungal infections caused by, for example, Candida spp., Aspergillus spp., or Scedosporium spp.

For clinical use, the novel Aerothricins of Formula (I) as well as pharmaceutically acceptable salts thereof can be administered alone, but will generally be administered in pharmaceutical admixture with a pharmaceutically acceptable carrier formulated as appropriate to the particular use and purpose desired, by mixing excipient, binding agent, lubricant, disintegrating agent, coating material, emulsifier, suspending agent, solvent, stabilizer, absorption enhancer and/or ointment base. The admixture can be used for oral, injectable, nasal, rectal or topical administration.

Pharmaceutical formulations of Aerothricins for oral administration may be granule, tablet, sugar coated tablet, capsule, pill, suspension or emulsion. For parenteral injection, for example, intravenously, intramuscularly or subcutaneously, Aerothricins of Formula (I) may be used in the form of a sterile aqueous solution which may contain other substances, for example, salts or glucose to make the solution isotonic. These compositions also may be presented in unit dosage form in ampoules or in multidose containers, preferable with added preservatives. Alternatively, the active ingredients may be in powder form for reconstituting with a suitable vehicle prior to administration. Aerothricins can also be administered in the form of a suppository or pessary, or they may be applied topically in the form of a lotion, solution, cream, ointment or dusting powder.

The daily dosage level of Aerothricins of Formula (I) is from 0.1 to 50 mg/kg (in divided doses) when administered by either the oral or parenteral route. Thus tablets or capsules of Aerothricins can be expected to contain from 5 mg to 0.5 g of active compound for administration singly or two or more at a time as appropriate. In any event the actual dosage can be determined by the physician and it may be varied upon the age, weight and response of the particular patient.

When Aerothricins are for antifungal use any method of administration may be employed. For treating mycotic infections, oral or intravenous administration is usually employed.

When Aerothricins are to be employed for control of pneumocystis infections it is desirable to directly treat lung and bronchi. For this reason inhalation methods are preferred. For administration by inhalation or nasal, Aerothricins of the present invention are conveniently delivered in the form of an aerosol spray presentation from pressurized packs or nebulisers. The preferred delivery system for inhalation or nasal is a metered dose inhalation aerosol, which may be formulated as a powder, suspension or solution of a compound of Formula (I) in suitable propellants, such as fluorocarbons or hydrocarbons.

Although Aerothricins of the present invention may be employed as tablets, capsules, topical compositions, insufflation powders, suppositories, and the like, the solubility of Aerothricins of the present invention in water and aqueous media render them adaptable for use in injectable formulations and also in liquid compositions suitable for aerosol sprays.

The following Examples illustrate the preferred methods for the preparation of Aerothricins of the present invention, which are not intended to limit the scope of the invention thereto.

In the following Examples, the products were analyzed and purified by HPLC using a reverse phase column selected from those listed below. The mixed solvent consisted of 0.05% trifluoroacetic acid-water: 0.05% trifluoroacetic acid-acetonitrile with the appropriate ratio described in each working Example.

| HPLC columns: | |
|---|---|
| Column A: | CAPCELL PAK C18, UG-120, 4.6 × 250 mm |
| Column B: | CAPCELL PAK C18, UG-120, 10 × 250 mm |
| Column C: | CAPCELL PAK C18, UG-80, 20 × 250 mm |
| Column D: | CAPCELL PAK C18, SG-120, 4.6 × 250 mm |
| Column E: | CAPCELL PAK C18, SG-120, 10 × 250 mm |
| Column F: | TSK GEL ODS-80Ts, 20 × 250 mm |

In the following working Examples, Aerothricins were obtained as trifluoroacetic acid salts unless otherwise indicated.

Reference Example 1

Preparation of Aerothricins 1, 2 and 3 a) Solid Fermentation

A 0.1 ml portion of the frozen culture of Deuteromycotina NR 7379 (FERM BP-6391) in 10% (v/v) glycerol solution was defrosted and inoculated into a 500-ml Erlenmeyer flask containing 100 ml of a medium consisting of 2% glucose, 1% potato starch, 1.5% glycerol, 1% Toast soya (Nissin Seiyu), 0.35% yeast extract (Nippon Seiyaku), 0.25% Polypepton (Nihon Seiyaku), 0.3% NaCl, 0.5% $CaCO_3$, 0.005% $ZnSO_4.7H_2O$, 0.0005% $CuSO_4.5H_2O$, and 0.0005% $MnSO_4.4H_2O$. The pH of the medium was not adjusted. The seed culture was incubated on a rotary shaker at 27° C. for 7 days at 220 rpm. 2 ml of the seed culture was transferred into a 3-liter Erlenmeyer flask containing a solid medium consisting of 200 g pressed barley, 0.12 g yeast extract (Difco), 0.06 g sodium tartarate, 0.06 g $KH_2PO_4$, and 120 ml water. The fermentation was carried out at 27° C. under static condition. The production reached maximum at around 240 h of fermentation and the culture was subjected to the isolation procedure of Aerothricins 1, 2 and 3.

The cultured solid (10 kg) obtained was added methanol (40 L) and the mixture was stirred, followed by removal filtration to obtain methanol extract (39 L). The methanol extract thus obtained was concentrated to dryness under reduced pressure, and the residue (64.8 g) was added ethyl acetate (1 L) and water (1 L). And the mixture was stirred, followed by removal of the ethyl acetate layer.

Furthermore, the aqueous layer was likewise washed with ethyl acetate (1 L) twice. The remaining aqueous layer was extracted with n-butanol (1 L) three times. The extracts thus obtained were combined and concentrated to dryness under reduced pressure, and the residue (28.5 g) was dissolved into a mixture (250 ml) of acetonitrile-0.1% aqueous trifluoroacetic acid (1:1). After removal of the insoluble materials by centrifugation, the solution thus obtained was evaporated to dryness under reduced pressure, and the residue was added methanol (300 ml) and the mixture was stirred, followed by removal filtration to obtain the methanol solution (280 ml). The methanol soluble materials (9.3 g) thus obtained were then subjected to a column chromatography on reversed phase silica gel C18 (1 L). The column was eluted stepwise using a mixture of methanol-0.1% aqueous trifluoroacetic acid (2:8, 4:6, 5:5, 6:4, 7:3, and 8:2). The Aerothricins 1, 2 and 3 eluted in this order with methanol-0.1% aqueous trifluoroacetic acid (7:3) were concentrated to dryness in vacuo to obtain white powdery Aerothricin 3 trifluoroacetic acid salt (731 mg) and Aerothricin 1 trifluoroacetic acid salt (747 mg), respectively. The fractions containing Aerothricin 2 was concentrated under reduced pressure and further purified by HPLC under the following conditions: column: Capcell Pak C18 (i.d. 30×250 mm, Shiseido Co., LTD.); mobile phase: acetonitrile-0.1% aqueous trifluoroacetic acid (45:55); flow rate: 40 ml/min.; detection: UV 220 nm. The appropriate eluates obtained under the above conditions were concentrated to dryness in vacuo to obtain white powdery Aerothricin 2 trifluoroacetic acid salt (42 mg).

b) Flask Fermentation

A 2 ml portion of the frozen culture of Deuteromycotina NR 7379 (FERM BP-6391) in 10% (v/v) glycerol solution was defrosted and inoculated into a 500-ml Erlenmeyer flask containing 100 ml of a medium consisting of 1% glucose, 1% oat flour, 4% tomato paste, 0.5% corn steep liquor (Ando kasei), 0.001% $FeSO_4.7H_2O$, 0.001% $MnSO_4.4H_2O$, 0.0001% $CaCl_2$, 0.0002% $ZnSO_4.7H_2O$, 0.00002% $(NH_4)6MoO_2.4H_2O$, and 0.00006% $H_3BO_3$. The pH of the medium was adjusted to 6.8 before sterilization. The seed culture was incubated on a rotary shaker at 27° C. for 3 days at 220 rpm. 2 ml of the first seed culture was transferred into 500-ml Erlenmeyer flasks containing 100 ml of the same medium and incubated on a rotary shaker under the same conditions for 3 days. 2 ml of the second seed culture was inoculated into 500-ml Erlenmeyer flasks containing 100 ml of the medium consisting of 8.5% glycerol, 1% pectin from citrus, 0.4% peanuts powder, 0.4% casein from milk vitamin-free, 0.4% tomato paste, 0.4% corn steep liquor (Ando kasei), 0.2% glycine, and 0.2% $KH_2PO_4$. The pH of the medium was adjusted to 7.0 before sterilization. The fermentation was conducted at 27° C. with agitation of 220 rpm. After 10 days cultivation, the production reached maximum and the whole culture was subjected to the isolation procedure of Aerothricins 1, 2 and 3.

c) Jar Fermentation

A 2 ml portion of the frozen culture of Deuteromycotina NR 7379 (FERM BP-6391) in 10% (v/v) glycerol solution was defrosted and inoculated into a 500-ml Erlenmeyer flask containing 100 ml of the same seed medium as described above. The flask was shaken at 220 rpm for 3 days at 27° C. 2 ml of the first seed culture was transferred into 500-ml Erlenmeyer flasks containing 100 ml of the same seed medium and incubated on a rotary shaker under the same conditions for 3 days. Six hundred ml of the second seed culture was inoculated into 50-liter jar fermentor containing 30 liters of the same production medium as described above and 0.4% disfoam (Nissan Disfoam CA-123). The fermentation was carried out at 27° C., with aeration of 30 liters/min. and agitation of 400 rpm. The production reached maximum at around 168 h of fermentation and the whole culture was subjected to the isolation procedure of Aerothricins 1, 2 and 3.

Aerothricin 1

Figure 2:
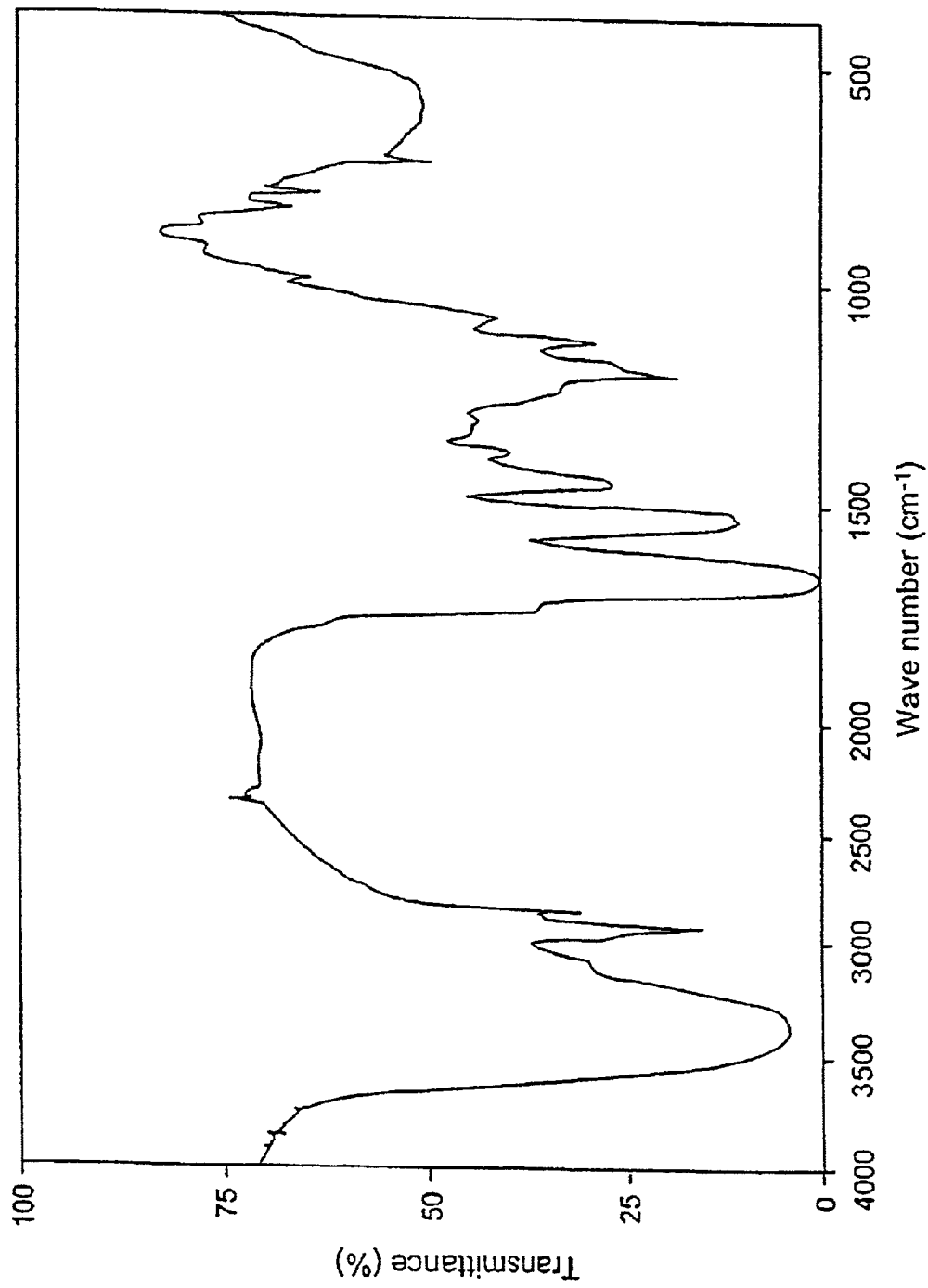
Figure 3:
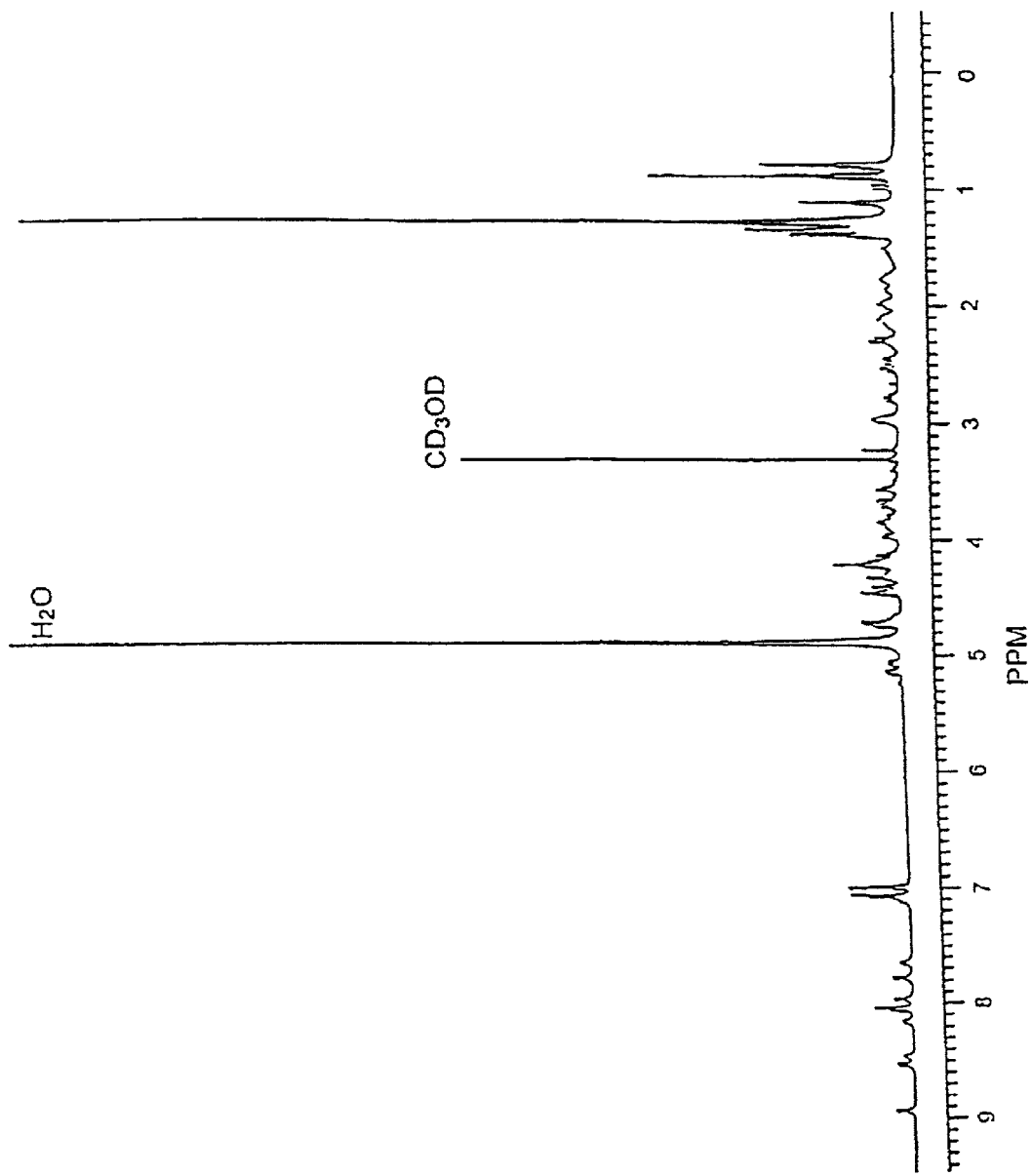
Figure 4:
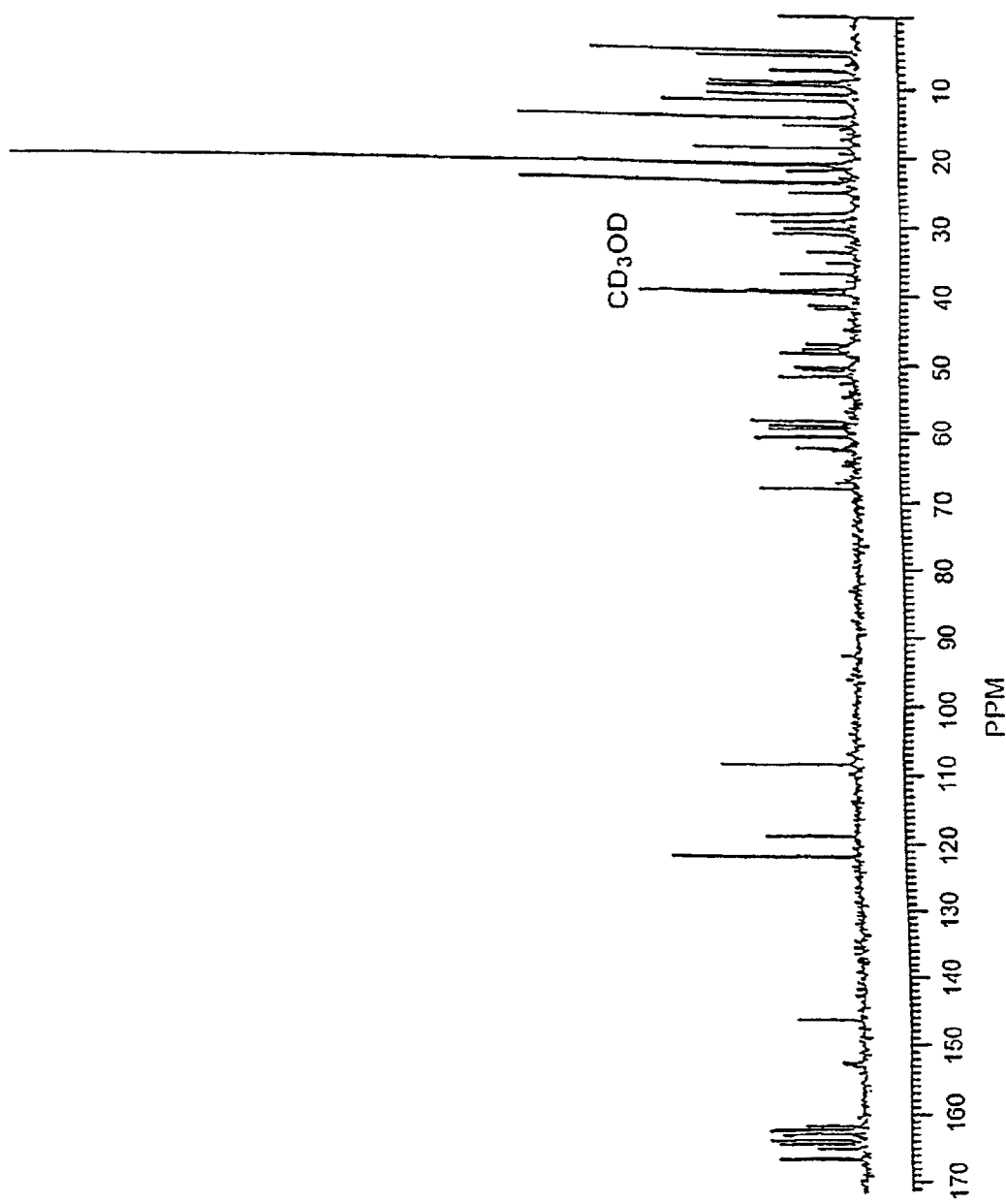

1) Appearance:
   white solid
2) Molecular weight (FAB-MS method):
   m/z 1547 (M+H)$^+$
3) Molecular formula:
   $C_{72}H_{118}N_{14}O_{23}$
4) High resolution mass spectroscopy (for M+H)$^+$:
   Found: 1547.8568
   Calculated for $C_{72}H_{119}N_{14}O_{23}$: 1547.8572
5) UV spectrum (FIG. 1): in methanol:
   $\lambda(\epsilon)$max (in MeOH): 225±5 (10600 sh), 270±5 (2000), 278±5 (2100)
   $\lambda(\epsilon)$max (in N/10 NaOH—MeOH): 240±5 (7700), 268±5 (1800), 298±5 (1800)
6) IR spectrum (KBr) (FIG. 2):
   Main absorption wave numbers (cm$^{-1}$) are as follows:
   3379, 2927, 2855, 1740, 1660, 1535, 1453, 1203, 1139, 837
7) $^1$H-NMR spectrum (FIG. 3):
   400 MHz, in $CD_3OD$
8) $^{13}$C-NMR spectrum (FIG. 4):
   100 MHz, in $CD_3OD$
9) Solubility:
   Soluble: water, methanol, dimethylsulfoxide
10) Color reaction:
    Positive: ninhydrin, anisaldehyde-sulfuric acid, iodine vapor, vanillin-sulfuric acid, Rydon-Smith reagent, molybdophosphoric acid
    Negative: Sakaguchi reagent, Bromocresol green, 2,4-dinitrophenylhydrazine-sulfuric acid
11) Thin-layer chromatography (TLC):

| Carrier | Solvent | Rf |
|---|---|---|
| silica gel F254*[1] | n-BuOH:acetone:AcOH:$H_2O$ (4:5:1:1) | 0.74 |
| | MeOH:$H_2O$ (95:5) | 0.12 |

*[1]E. Merck AG., Germany

12) High Performance Liquid Chromatography:
    Carrier: Capcell Pak C18 gel S120A, 4.6×250 mm (manufactured by Shiseido, Co., LTD.)
    Mobile phase: Acetonitrile: 0.05% aqueous trifluoroacetic acid=1:1
    Flow rate: 1 ml/min.
    Rt=12.1±0.5
13) Amino acid analysis:
    Aerothricin 1 was heated at 120° C. in 6N HCl for 24 h, followed by subjecting to amino acid analysis to detect threonine, 3 units of allo-threonine, glycine, alanine, valine, tyrosine, ornithine, 3-hydroxyproline, 4-hydroxyproline, 3-hydroxyglutamine.

Aerothricin 2

Figure 5:
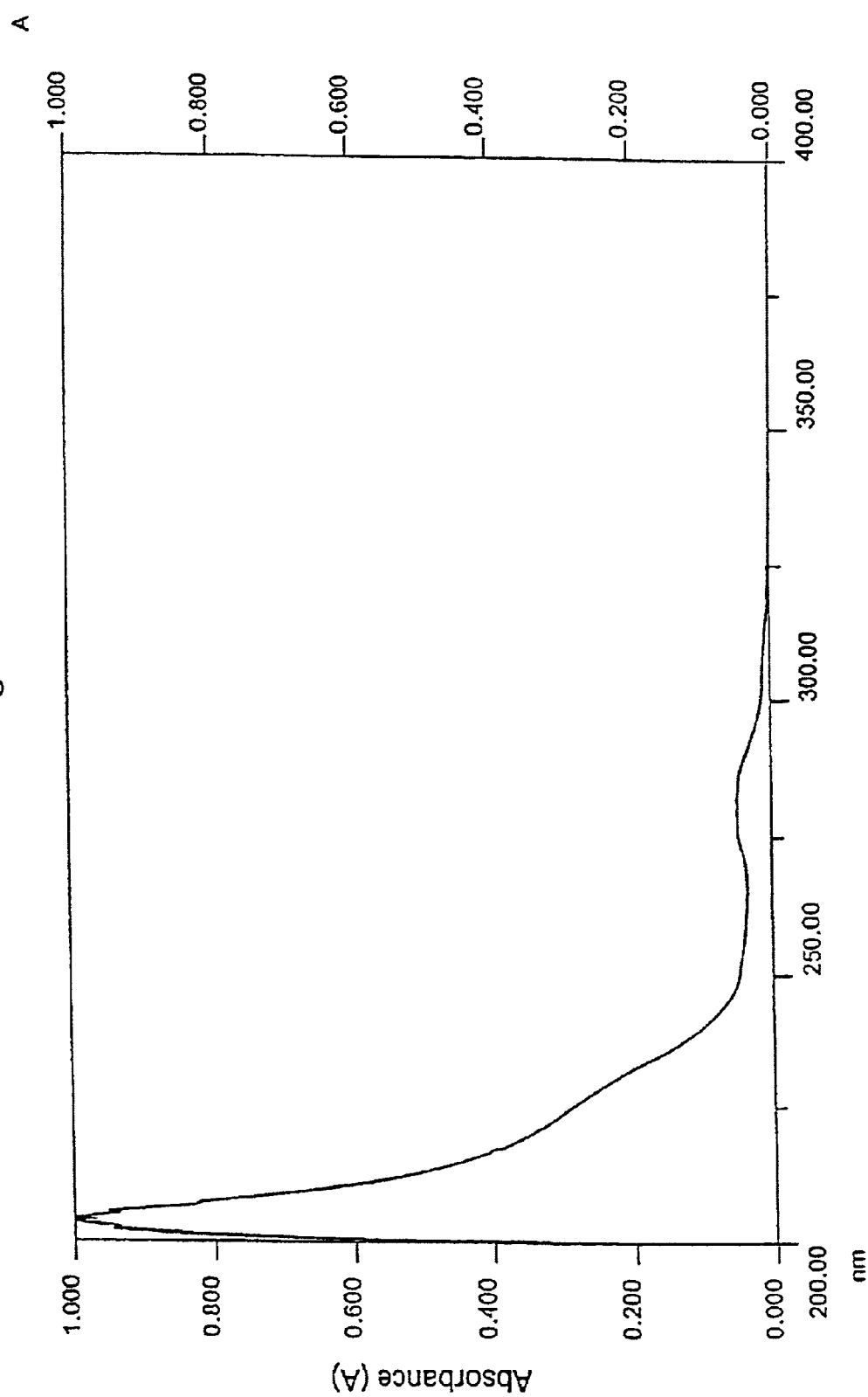
FIGS. 5–8 respectively show the UV, IR, $^1$H-NMR and $^{13}$C-NMR spectra plotted for the starting material Aerothricin 2 prepared in accordance with Reference Example 1.
Figure 6:
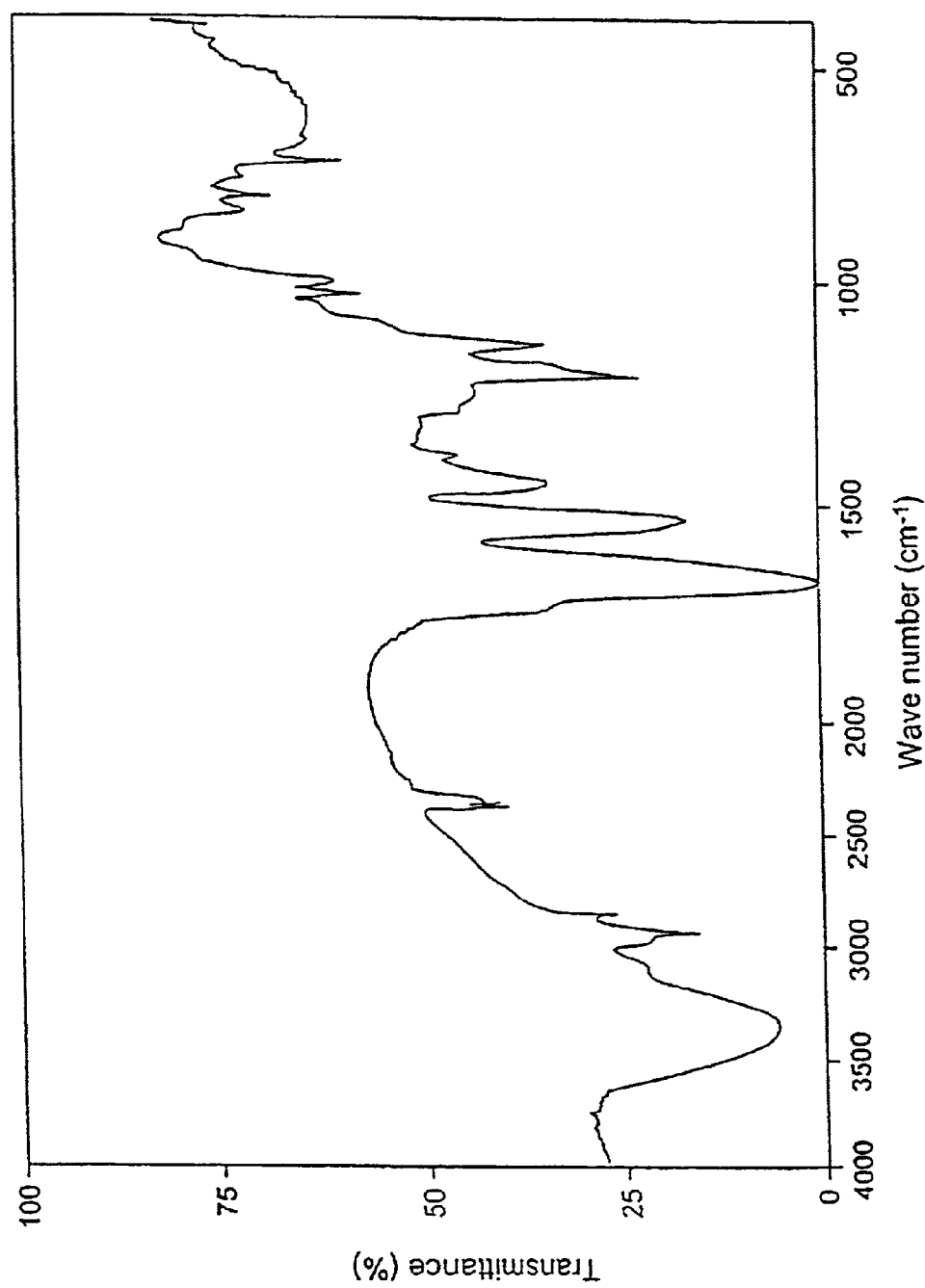
Figure 7:
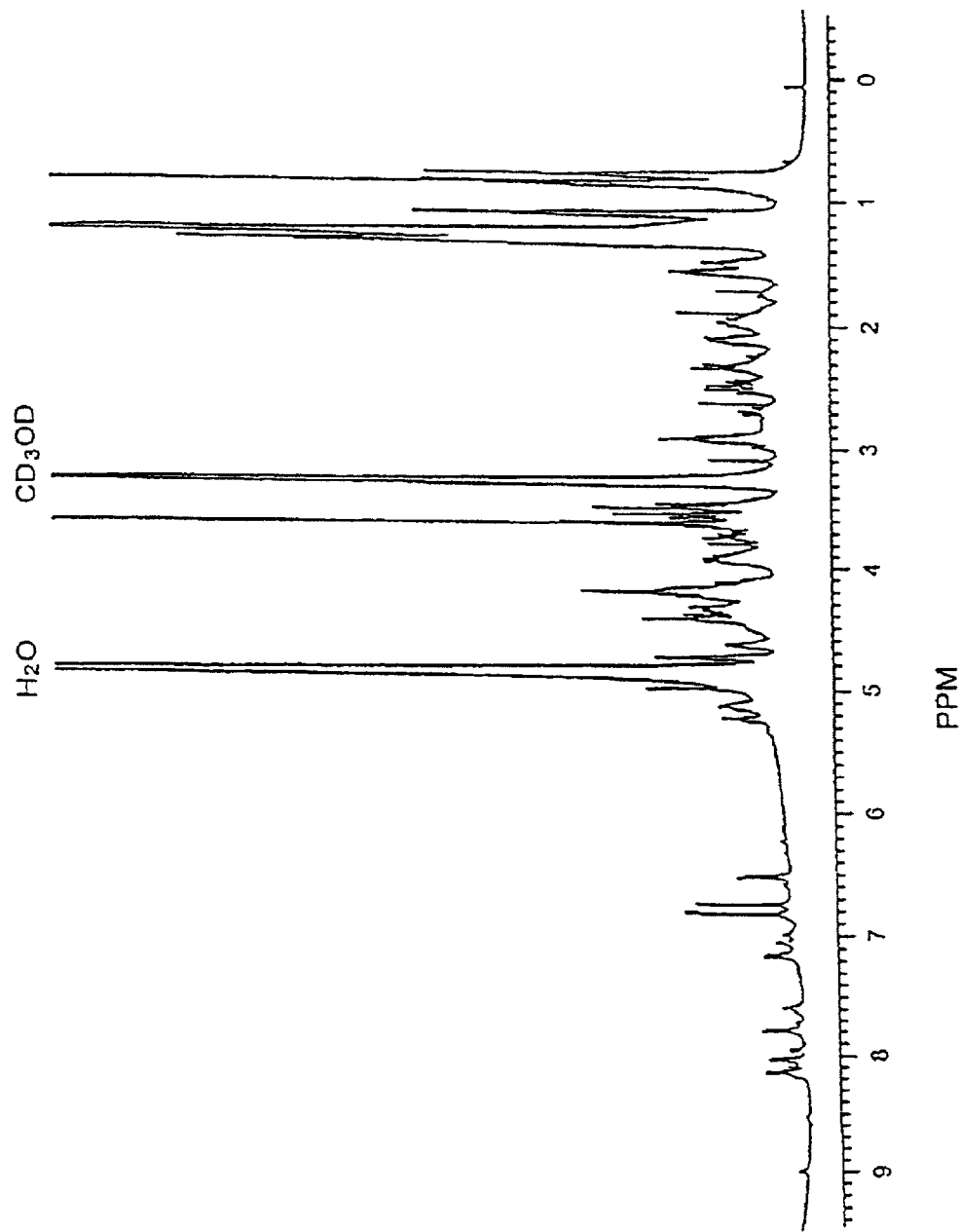
Figure 8:
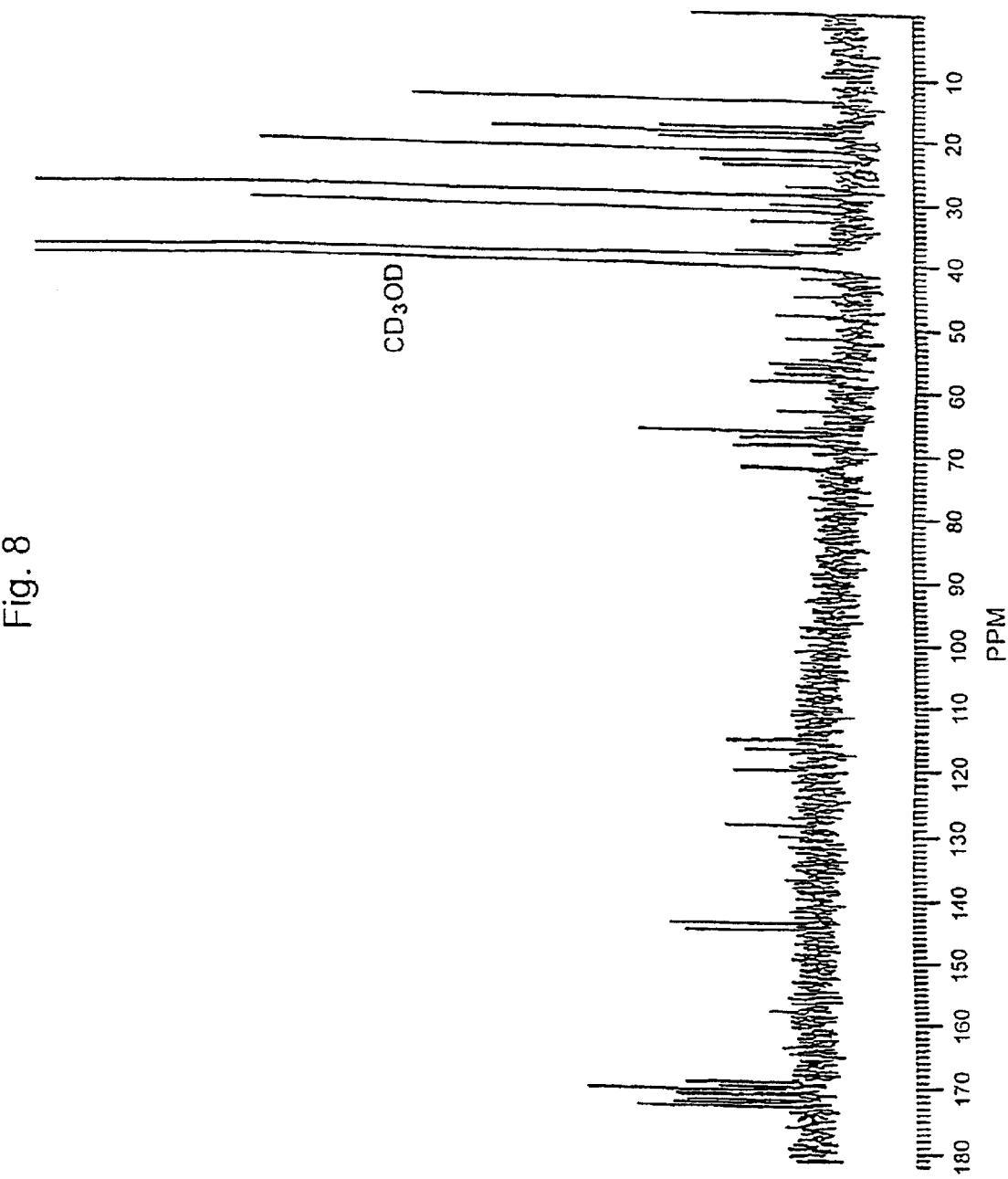

1) Appearance:
   white solid
2) Molecular weight (FAB-MS method):
   m/z 1549 (M+H)$^+$
3) Molecular formula:
   $C_{71}H_{116}N_{14}O_{24}$
4) High resolution mass spectroscopy (for M+H)$^+$:
   Found: 1549.8384
   Calculated for $C_{71}H_{117}N_{14}O_{24}$: 1549.8365
5) UV spectrum (FIG. 5): in methanol:
   $\lambda(\epsilon)$max (in MeOH): 225±5 (10200 sh), 275±5 (1900), 278±5 (2000)
   $\lambda(\epsilon)$max (in N/10 NaOH—MeOH): 240±5 (7700), 293±5 (2000)
6) IR spectrum (KBr) (FIG. 6):
   Main absorption wave numbers (cm$^{-1}$) are as follows:
   3323, 2928, 2856, 1740, 1670, 1531, 1450, 1203, 1137, 837
7) $^1$H-NMR spectrum (FIG. 7):
   400 MHz, in $CD_3OD$ 8) $^{13}$C-NMR spectrum (FIG. 8):
   100 MHz, in CD$_3$OD
9) Solubility:
   Soluble: water, methanol, dimethylsulfoxide
10) Color reaction:
   Positive: ninhydrin, anisaldehyde-sulfuric acid, Iodine vapor, vanillin-sulfuric acid, Rydon-Smith reagent, molybdophosphoric acid
   Negative: Sakaguchi reagent, bromocresol green, 2,4-dinitrophenylhydrazine-sulfuric acid
11) Thin-layer chromatography (TLC):

| Carrier | Solvent | Rf |
|---|---|---|
| Silica gel F254*[1] | n-BuOH:acetone:AcOH:H$_2$O (4:5:1:1) | 0.29 |
| | MeOH:H$_2$O (95:5) | 0.15 |

*[1]E. Merck AG., Germany

12) High Performance Liquid Chromatography:
   Carrier: Capcell Pak C18 gel S120A, 4.6×250 mm (manufactured by Shiseido, Co., LTD.)
   Mobile phase: Acetonitrile: 0.05% aqueous trifluoroacetic acid=1:1
   Flow rate: 1 ml/min.
   Rt=9.9±0.5
13) Amino acid analysis:
   Aerothricin 2 was heated at 120° C. in 6N HCl for 24 h, followed by subjecting to amino acid analysis to detect threonine, 3 units of allo-threonine, glycine, alanine, valine, 3-hydroxytyrosml (DOPA), ornithine, 3-hydroxyproline, 4-hydroxyproline, 3-hydroxyglutamine.

Aerothricin 3
1) Appearance:
   white solid
2) Molecular weight (FAB-MS method):
   m/z 1533 (M+H)$^+$
3) Molecular formula:
   C$_{71}$H$_{116}$N$_{14}$O$_{23}$
4) UV spectrum: in methanol
   λ(ε)max (in MeOH): 225±5 (11000 sh), 275±5 (2000), 280±5 (1900)
   λ(ε)max (in N/10 NaOH—MeOH): 243±5 (7800), 295±5 (1800)
5) IR spectrum (KBr):
   Main absorption wave numbers (cm$^{-1}$) are as follows:
   3334, 2928, 2852, 1742, 1662, 1520, 1449, 1202, 1136, 836
6) Solubility:
   Soluble: water, methanol, dimethylsulfoxide
7) Color reaction:
   Positive: ninhydrin, anisaldehyde-sulfuric acid, Iodine vapor, vanillin-sulfuric acid, Rydon-Smith reagent, molybdophosphoric acid
   Negative: Sakaguchi reagent, bromocresol green, 2,4-dinitrophenylhydrazine-sulfuric acid
8) Thin-layer chromatography (TLC):

| Carrier | Solvent | Rf |
|---|---|---|
| silica gel F254*[1] | n-BuOH:acetone:AcOH:H$_2$O (4:5:1:1) | 0.26 |
| | MeOH:H$_2$O (95:5) | 0.09 |

*[1]E. Merck AG., Germany

9) High Performance Liquid Chromatography:
   Carrier: Capcell Pak C18 gel S120A, 4.6×250 mm (manufactured by Shiseido, Co., LTD.)
   Mobile phase: Acetonitrile: 0.05% aqueous trifluoroacetic acid=1:1
   Flow rate: 1 ml/min.
   Rt=9.1±0.5
10) Amino acid analysis:
   Aerothricin 3 was heated at 120° C. in 6N HCl for 24 h, followed by subjecting to amino acid analysis to detect threonine, 3 units of allo-threonine, glycine, alanine, valine, tyrosine, ornithine, 3-hydroxyproline, 4-hydroxyproline, 3-hydroxyglutamine.

EXAMPLE 1

Preparation of Aerothricin 132

(a) To a mixture of Aerothricin 3 (500 mg, 0.326 mmol) and triethylamine (682 μl, 4.89 mmol) in MeOH (10 ml) was added acrylonitrile (214 μl, 3.27 mmol) at room temperature. The mixture was stirred for 20 hours at room temperature. After the solvent was evaporated in vacuo, the residue was dissolved in n-butanol and washed with diluted hydrochloric acid and water successively. The organic layer was evaporated in vacuo. The crude residue was purified by preparative reverse HPLC, the detailed condition of which is shown below. The appropriate fraction were combined, frozen and lyophilized to give 207 mg of Aerothricin 120 (compound of Formula (I), wherein R$^2$ and R$^3$ are hydrogen and R$^1$ is (2-cyanoethyl)-amino) as a colorless amorphous solid.

HPLC(Rt) 27.5 min (column F, flow rate: 10 ml/min, eluent: 0.05% Trifluoroacetic acid: 0.05% Trifluoroacetic acid-Acetonitrile=53:47); FAB-MS (m/z) 1586 [M+H]$^+$.

(b) To a stirred solution of Boc-L-Orn(Boc)-OH (46 mg, 0.138 mmol) in DMF (2 ml) were added BOP reagent (62 mg, 0.14 mmol), HOBT hydrate (22 mg, 0.144 mmol) and N-ethyldiisopropylamine (24 μl, 0.138 mmol ). After being stirred for 2 h at room temperature, a solution of Aerothricin 120 (100 mg, 0.063 mmol) and N-ethyldiisopropylamine (24 μl, 0.138 mmol ) in DMF (2 ml) was added to the reaction mixture. After being stirred for 20 h at room temperature, the solvent was evaporated in vacuo.

A solution of the crude residue obtained above in TFA (3 ml) was stirred at 0° C. for 30 min. The reaction vessel was opened and TFA was evaporated under a stream of dry nitrogen. The residue was purified by preparative reverse phase HPLC, the detailed condition of which is shown below. The pure fractions were combined, frozen and lyophilized to give 60.5 mg of the compound-1 as a white amorphous solid.

HPLC(Rt) 20.7 min (column F, flow rate: 10 ml/min, eluent: 0.05% Trifluoroacetic acid: 0.05% Trifluoroacetic acid-Acetonitrile=57:43); FAB-MS (m/z): 1700 [M+H]$^+$.

(c) To a mixture of the compound-1 (60.5 mg, 0.0356 mmol) in dioxane (2 ml) and water (2 ml) was added 10% palladium on charcoal (10 mg), and the reaction vessel was filled with hydrogen. After being stirred for 14 hours at room temperature, the mixture was filtered through membrane filter (pore size: 0.2 mm) and the solvent was evaporated in vacuo. The crude residue was purified by preparative reverse HPLC, the detailed condition of which is shown below. The appropriate fraction were combined, frozen and lyophilized to give 27.8 mg of Aerothricin 132 as a colorless amorphous solid.

HPLC(Rt) 18.9 min (column F, flow rate: 10 ml/min, eluent: 0.05% Trifluoroacetic acid: 0.05% Trifluoroacetic acid-Acetonitrile=60:40); FAB-MS (m/z): 1704 [M+H]$^+$.

EXAMPLE 2
Preparation of Aerothricin 134

(a) To a stirred solution of Fmoc-L-Orn(Boc)-OH (379 mg, 0.834 mmol) in DMF (6 ml) were added BOP reagent (368 mg, 0.832 mmol), HOBT hydrate (128 mg, 0.836 mmol) and N-ethyldiisopropylamine (145 μl, 0.832 mmol ). After being stirred for 2 h at room temperature, a solution of Aerothricin 120 (600 mg, 0.378 mmol) and N-ethyldiisopropylamine (145 μl, 0.832 mmol ) in DMF (3 ml) was added to the reaction mixture. After being stirred for 18 h at room temperature, piperidine (3 ml) was added to the mixture. The reaction mixture was stirred for 10 minutes at room temperature. The solvent was evaporated in vacuo. The residue was washed with dichloromethane and diethylether to remove the reagents. The crude product was used for the next step without further purification.

(b) To a solution of the crude product (320 mg) obtained above in MeOH (10 ml) were added (2-oxo-ethyl)carbamic acid tert-butylester (crude, 530 mg), AcOH (2 ml) and NaBH$_3$CN (210 mg, 3.342 mmol) in MeOH (4 ml). After the mixture was stirred for 20 h at room temperature, the reaction mixture was concentrated in vacuo. The residue was dissolved in n-butanol and washed with diluted hydrochloric acid and water successively. The organic layer was evaporated in vacuo.

A solution of the crude residue obtained above in TFA (6 ml) was stirred at 0° C. for 30 min. The reaction vessel was opened and TFA was evaporated under a stream of dry nitrogen. The residue was purified by preparative reverse HPLC, the detailed condition of which is shown below. The appropriate fraction were combined, frozen and lyophilized to give 88.2 mg of the compound-2 as a white amorphous solid.

HPLC(Rt) 22.4 min (column F, flow rate: 10 ml/min, eluent: 0.05% Trifluoroacetic acid: 0.05% Trifluoroacetic acid-Acetonitrile=60:40)

(c) To a mixture of the compound-2 (88.2 mg, 0.0494 mmol) in dioxane (1.5 ml) and water (1.5 ml) was added 10% palladium on charcoal (20 mg), and the reaction vessel was filled with hydrogen. After being stirred for 16 hours at room temperature, the mixture was filtered through membrane filter (pore size: 0.2 mm) and the solvent was evaporated in vacuo. The crude residue was purified by preparative reverse HPLC, the detailed condition of which is shown below. The appropriate fraction were combined, frozen and lyophilized to give 22.0 mg of Aerothricin 134 as a colorless amorphous solid.

HPLC(Rt) 25.7 min (column F, flow rate: 10 ml/min, eluent: 0.05% Trifluoroacetic acid: 0.05% Trifluoroacetic acid-Acetonitrile=63:37); FAB-MS (m/z) 1790 [M+H]$^+$.

EXAMPLE 3
Preparation of Aerothricin 135

Aerothricin 135 was prepared according to the method similar to that described In Example 2:

HPLC(Rt) 25.5 min (column F, flow rate: 10 ml/min, eluent: 0.05% Trifluoroacetic acid: 0.05% Trifluoroacetic acid-Acetonitrile=63:37); FAB-MS (m/z) 1790 [M+H]$^+$.

EXAMPLE 4
Preparation of Aerothricin 136

(a) To a stirred solution of Fmoc-L-Orn(Boc)-OH (379 mg, 0.834 mmol) in DMF (6 ml) were added BOP reagent (368 mg, 0.832 mmol), HOBT hydrate (128 mg, 0.836 mmol) and N-ethyldiisopropylamine (145 μl, 0.832 mmol ). After being stirred for 2 h at room temperature, a solution of Aerothricin 120 (600 mg, 0.378 mmol) and N-ethyldiisopropylamine (145 μl, 0.832 mmol ) in DMF (3 ml) was added to the reaction mixture. After being stirred for 18 h at room temperature, piperidine (3 ml) was added to the mixture. The reaction mixture was stirred for 10 minutes at room temperature. The solvent was evaporated in vacuo. The residue was washed with dichloromethane and diethylether to remove the reagents. The crude product was used for the next step without further purification.

(b) To a solution of the crude product (300 mg) obtained above in EeOH (10 ml) were added acrylonitrile (110 μl, 1.68 mmol) and N-ethyldiisopropylamine (44 μl, 0.253 mmol). After the mixture was stirred for 14 h at room temperature, acrylonitrile (440 μl, 6.72 mmol) and N-ethyldiisopropylamine (44 μl, 0.253 mmol ) were added. After the mixture was stirred for 22 h at room temperature, acrylonitrile (220 μl, 3.36 mmol) and N-ethyldiisopropylamine (44 μl, 0.253 mmol ) were added . After the mixture was stirred for 6 h at room temperature, the reaction mixture was concentrated in vacuo. The residue was washed with dichloromethane and diethylether to remove the reagents.

A solution of the crude residue obtained above in TFA (3 ml) was stirred at 0° C. for 30 min. The reaction vessel was opened and TFA was evaporated under a stream of dry nitrogen. The residue was purified by preparative reverse HPLC, the detailed condition of which is shown below. The appropriate fraction were combined, frozen and lyophilized to give 104.6 mg of the compound-3 as a white amorphous solid.

HPLC(Rt) 27.8 min (column F, flow rate: 10 ml/min, eluent: 0.05% Trifluoroacetic acid: 0.05% Trifluoroacetic acid-Acetonitrile=57:43)

(c) To a mixture of the compound-3 (104.6 mg, 0.0596 mmol) in dioxane (3 ml) and water (3 ml) was added 10% palladium on charcoal (25 mg), and the reaction vessel was filled with hydrogen. After being stirred for 16 hours at room temperature, the mixture was filtered through membrane filter (pore size: 0.2 mm) and the solvent was evaporated in vacuo. The crude residue was purified by preparative reverse HPLC, the detailed condition of which is shown below. The appropriate fraction were combined, frozen and lyophilized to give 40.3 mg of Aerothricin 136 as a colorless amorphous solid.

HPLC(Rt) 25.8 min (column F, flow rate: 10 ml/min, eluent: 0.05% Trifluoroacetic acid: 0.05% Trifluoroacetic acid-Acetonitrile=63:37); FAB-MS (m/z): 1761 [M+H]$^+$.

EXAMPLE 5
Preparation of Aerothricin 133

(a) To a solution of Aerothricin 3 monoTFA salt (2.5 g) in DMF (10 ml) was added Fmoc-D-Orn(Boc)OH (850 mg), BOP (180 mg), HOBT (279 mg) and N-ethyldiisopropylamine (0.795 ml). After the mixture being stirred for 3 hrs. at room temperature, piperidine (4.0 ml) was added. The stirring was continued for 30 min. at room temperature, and then the solvent was evaporated in vacuo. The residue was dissolved in dichloromethane, and dropwise addition of ether gave the crude product as white amorphous powder. It was washed with ether and used in the next step without further purification.

(b) The crude product obtained above was dissolved in DMF (20 ml). To this solution was added Boc-L-Orn(Boc) OH (656 mg), BOP (872 mg), HOBT (302 mg) and N-ethyldiisopropylamine (0.793 ml). After the mixture was stirred for 3 hrs. at room temperature, the solvent was evaporated in vacuo.

(c) TFA (15 ml) was added at 0° C. to the residue obtained above. After the mixture was stirred for 30 min. at 0° C., ether was added dropwise to give a white precipitate. It was washed with ether and purified by preparative reverse phase HPLC. The pure fractions were combined, frozen and lyophilized to give 515 mg of Aerothricin 133 as a colorless amorphous solid:

HPLC(Rt): 19.7 min. (column F, flow rate: 10 ml/min., eluent: 0.05% trifluoroacetic acid-water: 0.05% trifluoroacetic acid-acetonitrile=60:40); FAB-MS (m/z): 1761 [MH$^+$].

EXAMPLE 6

Preparation of Aerothricin 137

(a) To a solution of Aerothricin 3 monoTFA salt (622 mg) in dichloromethane (16 ml) a MeOH (4 ml) was added N-Boc-aminoethanal (120 mg) and N-ethyldiisopropylamine (0.072 ml). After being stirred for 1 hr at room temperature, to the reaction mixture was added sodium cyanoborohydride (48 mg) and sulfuric acid (0.04 ml). After the reaction mixture was stirred for 72 hr at room temperature, the solvent was evaporated in vacuo and then 0.1N HCl was added. It was extracted with nBuOH and concentrated.

(b) The residue was dissolved in DMF (6 ml), to which was added 2-(S)-[bis-(2-Boc-aminoethyl)amino]-5-Boc-aminopentanoic acid (294 mg), HOAt (77 mg), HBTU (215 mg) and N-ethyldiisopropylamine (0.148 ml). After being stirred for 48 hr at room temperature, the solvent was evaporated in vacuo and the residue was dissolved in dichloromethane. To this solution was added ether to give a white precipitate. It was washed with ether and used in the next step without further purification.

(c) To the compound obtained above was then added TFA (3 ml) at 0° C. After being stirred for 30 min. at 0° C., ether was added to the reaction mixture to give a white precipitate. It was washed with ether and purified by preparative reverse phase HPLC. The pure fractions were combined, frozen and lyophilized to give 95 mg of Aerothricin 137 as a colorless amorphous solid:

HPLC(Rt): 14.6 min. (column F. flow rate: 10 ml/min., eluent: 0.05% trifluoroacetic acid-water: 0.05% trifluoroacetic acid-acetonitrile=61:39); FAB-MS (m/z): 1776 [M+H]$^+$.

EXAMPLE A

Injectable solutions each containing the following ingredients were manufactured in the conventional manner per se:

| | |
|---|---|
| Aerothricin 132 | 20 mg |
| di-Sodium hydrogenphosphate, anhydrous | 7.6 mg |
| Sodium diphosphate dihydrate | 2.0 mg |
| Ethyl alcohol | 150 mg |
| Distilled water, deionized, sterile | 850 mg |
| Total | 1029.6 mg |

What is claimed is:
1. A compound of the formula:

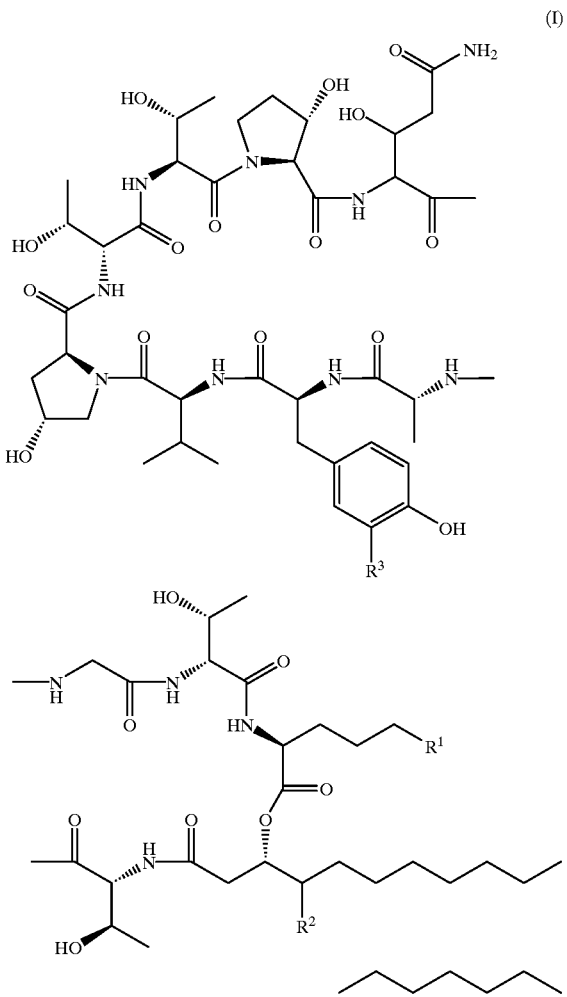

(I)

wherein
R$^1$ is N-(3-aminopropyl)-N-[(2S)-2,5-diaminovaleryl] amino, N-(3-aminopropyl)-N-[-5-amino-2-[N,N-bis(2-aminoethyl)amino]valeryl]amino, N-(3-aminopropyl)-N-[-5-amino-2-[N-(3-aminopropyl)amino]valeryl] amino, N-(2-aminoethyl)-N-[-5-amino-2-[N,N-bis(2-aminoethyl)amino]valeryl]amino or ornityl-ornitylamino;

R$^2$ is hydrogen or methyl;

R$^3$ is hydrogen or hydroxy;

or a pharmaceutically acceptable salt thereof.

2. The compound according to claim 1, wherein R$^1$ is N-(3-aminopropyl)-N-[(2S)-2,5-diaminovaleryl]amino, N-(3-aminopropyl)-N-[(2S)-5-amino-2-[N,N-bis(2-aminoethyl)amino]valeryl]amino, N-(3-aminopropyl)-N-[(2R)-5-amino-2-[N,N-bis(2-aminoethyl)amino]valeryl] amino, N-(3-aminopropyl)-N-[(2S)-5-amino-2-[N-(3-aminopropyl)amino]valeryl]amino, N-(2-aminoethyl)-N-[(2S)-5-amino-2-[N,N-bis(2-amino)amino]aleryl]amino, or (L)-ornityl-(D)-ornitylamino.

3. The compound according to claim 1, wherein R$^2$ and R$^3$ are hydrogen.

4. The compound according to claim 1, wherein R$^1$ is N-(3-aminopropyl)-N-[(2S)2,5-diaminovaleryl]amino, and R$^2$ and R$^3$ are hydrogen.

5. The compound according to claim 1, wherein $R^1$ is (L)-ornityl-(D)-ornitylamino, and $R^2$ and $R^3$ are hydrogen.

6. The compound according to claim 1, wherein $R^1$ is N-(3-aminopropyl)-N-[(2S)-5-amino-2-[N,N,-bis(2-aminoethyl)amino]valeryl]amino, and $R^2$ and $R^3$ are hydrogen.

7. The compound according to claim 1, wherein $R^1$ is N-(3-aminopropyl)-N-[(2R)-5-amino-2-[N,N-bis(2-aminoethyl)amino]valeryl]amino, and $R^2$ and $R^3$ are hydrogen.

8. The compound according to claim 1, wherein $R^1$ is N-(3-aminopropyl)-N-[(2S)-5-amino-2-[N-(3-aminopropyl)amino]valeryl]amino, and $R^2$ and $R^3$ are hydrogen.

9. The compound according to any of claims 1 to 3, wherein $R^1$ is N-(2-aminoethyl)-N-[(2S)-5-amino-2-[N,N-bis(2-aminoethyl)aminol]valeryl]amino, and $R^2$ and $R^3$ are hydrogen.

10. The compound according to claim 1 wherein $R^2$ is methyl and $R^3$ is hydrogen.

11. The compound according to claim 1 wherein $R^2$ is hydrogen and $R^3$ is hydroxyl.

12. A pharmaceutical composition comprising a mixture of a pharmaceutically acceptable carrier and an effective amount of a compound of the formula:

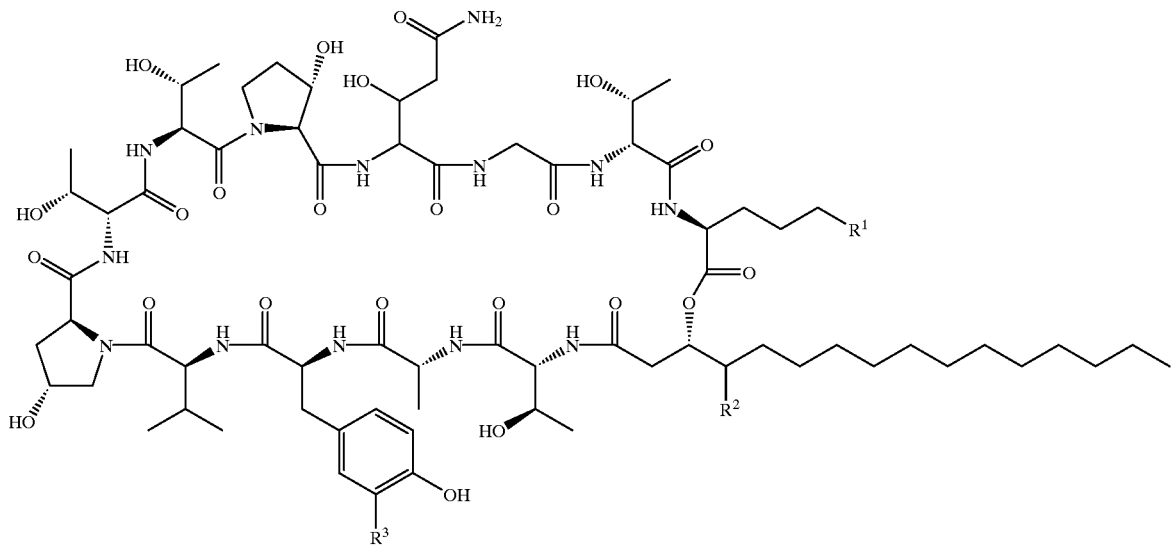

(I)

wherein
$R^1$ is N-(3-aminopropyl)-N-[(2S)-2,5-diaminovaleryl]amino, N-(3-aminopropyl)-N-[5-amino-2-[N,N-bis(2-aminoethyl)amino]valeryl]amino, N-(3-aminopropyl)-N-[-5-amino-2-[N-(3-aminopropyl)amino]valeryl]amino, N-(2-aminoethyl)-N-[-5-amino-2-[N,N-bis(2-aminoethyl)amino]valeryl]amino or ornityl-ornitylamino;

$R^2$ is hydrogen or methyl;

$R^3$ is hydrogen or hydroxy;

or a pharmaceutically acceptable salt thereof.

13. A method for the prophylactic and/or therapeutic treatment of mycoses which comprises administering to a human being or an animal an effective amount of the compound of the formula:

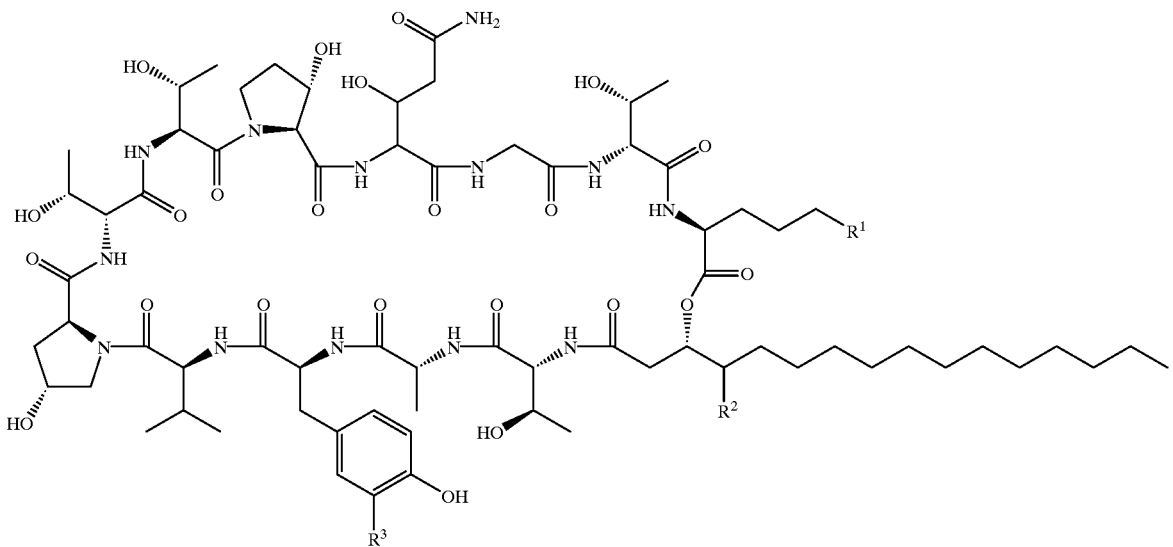

(I)

wherein

R¹ is N-(3-aminopropyl)-N-[(2S)-2,5-diaminovaleryl]amino, N-(3-aminopropyl)-N-[5-amino-2-[N,N-bis(2-aminoethyl)amino]valeryl]amino, N-(3-aminopropyl)-N-[5-amino-2-[N-(3-aminopropyl)amino]valeryl]amino, N-(2-aminoethyl)-N-[5-amino-2-[N,N-bis(2-aminoethyl)amino]valeryl]amino or ornityl-ornitylamino;

R² is hydrogen or methyl;

R³ is hydrogen or hydroxy;

or a pharmaceutically acceptable salt thereof, thereby producing antifungal activity.

* * * * *